US008431242B2

(12) United States Patent
Begley et al.

(10) Patent No.: US 8,431,242 B2
(45) Date of Patent: Apr. 30, 2013

(54) OLED DEVICE WITH CERTAIN FLUORANTHENE HOST

(75) Inventors: William J. Begley, Webster, NY (US); Tukaram K. Hatwar, Penfield, NY (US); Natasha Andrievsky, Webster, NY (US)

(73) Assignee: Global OLED Technology, LLC., Wilmington, DE (US)

( * ) Notice: Subject to any disclaimer, the term of this patent is extended or adjusted under 35 U.S.C. 154(b) by 1205 days.

(21) Appl. No.: 11/924,626

(22) Filed: Oct. 26, 2007

(65) Prior Publication Data
US 2009/0110957 A1   Apr. 30, 2009

(51) Int. Cl.
*H01L 51/54* (2006.01)
(52) U.S. Cl.
USPC ........... 428/690; 428/917; 313/504; 313/506; 252/301.16; 257/40
(58) Field of Classification Search .................. None
See application file for complete search history.

(56) References Cited

U.S. PATENT DOCUMENTS

| | | |
|---|---|---|
| 3,172,862 A | 3/1965 | Gurnee et al. |
| 3,173,050 A | 3/1965 | Gurnee |
| 3,180,730 A | 4/1965 | Klupfel et al. |
| 3,567,450 A | 3/1971 | Brantly et al. |
| 3,658,520 A | 4/1972 | Brantly et al. |
| 3,710,167 A | 1/1973 | Dresner |
| 4,356,429 A | 10/1982 | Tang |
| 4,539,507 A | 9/1985 | Vanslyke et al. |
| 4,720,432 A | 1/1988 | Vanslyke et al. |
| 4,768,292 A | 9/1988 | Manzei et al. |
| 4,769,292 A | 9/1988 | Tang et al. |
| 4,885,211 A | 12/1989 | Tang et al. |
| 4,885,221 A | 12/1989 | Tsuneeda et al. |
| 5,059,861 A | 10/1991 | Littman et al. |
| 5,059,862 A | 10/1991 | Vanslyke et al. |
| 5,061,569 A | 10/1991 | Vanslyke et al. |
| 5,121,029 A | 6/1992 | Hosokawa et al. |
| 5,141,671 A | 8/1992 | Bryan et al. |
| 5,150,006 A | 9/1992 | Van Slyke et al. |
| 5,151,629 A | 9/1992 | Van Slyke et al. |
| 5,247,190 A | 9/1993 | Friend et al. |
| 5,276,380 A | 1/1994 | Tang |
| 5,294,870 A | 3/1994 | Tang et al. |
| 5,405,709 A | 4/1995 | Littman et al. |
| 5,409,783 A | 4/1995 | Tang et al. |
| 5,484,922 A | 1/1996 | Moore et al. |
| 5,552,678 A | 9/1996 | Tang et al. |
| 5,554,450 A | 9/1996 | Shi et al. |
| 5,593,788 A | 1/1997 | Shi et al. |
| 5,608,287 A | 3/1997 | Hung et al. |
| 5,645,948 A | 7/1997 | Shi et al. |
| 5,677,572 A | 10/1997 | Hung et al. |
| 5,683,823 A | 11/1997 | Shi et al. |
| 5,688,551 A | 11/1997 | Littman et al. |
| 5,703,436 A | 12/1997 | Forrest et al. |
| 5,714,838 A | 2/1998 | Haight et al. |
| 5,739,545 A | 4/1998 | Guha et al. |
| 5,755,999 A | 5/1998 | Shi et al. |
| 5,766,779 A | 6/1998 | Shi et al. |
| 5,776,622 A | 7/1998 | Hung et al. |
| 5,776,623 A | 7/1998 | Hung et al. |
| 5,837,391 A | 11/1998 | Utsugi |
| 5,851,709 A | 12/1998 | Grande et al. |
| 5,908,581 A | 6/1999 | Chen et al. |
| 5,927,247 A | 7/1999 | Tanaka |
| 5,928,802 A | 7/1999 | Shi et al. |
| 5,935,720 A | 8/1999 | Chen et al. |
| 5,935,721 A | 8/1999 | Shi et al. |
| 5,969,474 A | 10/1999 | Arai |
| 5,981,306 A | 11/1999 | Burrows et al. |
| 6,020,078 A | 2/2000 | Chen et al. |
| 6,066,357 A | 5/2000 | Tang et al. |
| 6,097,147 A | 8/2000 | Baldo et al. |
| 6,137,223 A | 10/2000 | Hung et al. |
| 6,140,763 A | 10/2000 | Hung et al. |
| 6,172,459 B1 | 1/2001 | Hung et al. |
| 6,208,075 B1 | 3/2001 | Hung et al. |
| 6,208,077 B1 | 3/2001 | Hung |
| 6,226,890 B1 | 5/2001 | Boroson et al. |
| 6,237,529 B1 | 5/2001 | Spahn et al. |
| 6,278,236 B1 | 8/2001 | Madathil et al. |
| 6,284,393 B1 | 9/2001 | Hosokawa et al. |
| 6,337,492 B1 | 1/2002 | Jones et al. |
| 6,361,886 B2 * | 3/2002 | Shi et al. .................. 428/690 |
| 6,396,209 B1 | 5/2002 | Kido et al. |
| 6,423,429 B2 | 7/2002 | Kido et al. |
| 6,468,676 B1 | 10/2002 | Ueda et al. |
| 6,509,109 B1 | 1/2003 | Nakamura |
| 6,613,454 B2 | 9/2003 | Ara et al. |
| 6,661,023 B2 | 12/2003 | Hoag et al. |
| 6,689,493 B2 | 2/2004 | Motomatsu et al. |
| 6,720,092 B2 | 4/2004 | Hatwar |
| 6,720,573 B2 | 4/2004 | Son et al. |
| 6,773,832 B2 | 8/2004 | Sotoyama et al. |
| 6,803,120 B2 | 10/2004 | Fukuoka et al. |
| 6,824,895 B1 | 11/2004 | Sowinski et al. |
| 6,866,947 B1 | 3/2005 | Fukuoka et al. |

(Continued)

FOREIGN PATENT DOCUMENTS

| | | |
|---|---|---|
| EP | 0 141 403 | 5/1985 |
| EP | 681 019 | 11/1995 |

(Continued)

OTHER PUBLICATIONS

Dresner, "Double Injection Electroluminescence in Anthracene", RCA Review, 30, 322, 1969.

(Continued)

*Primary Examiner* — Michael H Wilson
(74) *Attorney, Agent, or Firm* — McKenna, Long & Aldridge, LLP.

(57) ABSTRACT

An OLED device comprises a cathode, an anode, and has therebetween: (a) a light emitting layer containing a non-light-emitting fluoranthene compound with a 7,10-diaryl substituted fluoranthene nucleus having no aromatic rings annulated to the fluoranthene nucleus; and (b) comprising still further an additional layer, containing an organic alkali metal compound, located between the cathode and the electron transporting layer. OLED devices of the invention provide reduced drive voltage and improved color, and provide embodiments with other improved features such as operational stability and high luminance.

15 Claims, 6 Drawing Sheets

U.S. PATENT DOCUMENTS

| | | | |
|---|---|---|---|
| 6,927,537 | B2 | 8/2005 | Takahashi |
| 6,936,961 | B2 | 8/2005 | Liao et al. |
| 7,165,340 | B2 | 1/2007 | Long et al. |
| 7,175,922 | B2 | 2/2007 | Jarikov |
| 7,183,010 | B2 | 2/2007 | Jarikov |
| 7,189,989 | B2 | 3/2007 | Ise |
| 7,221,088 | B2 | 5/2007 | Kafafi et al. |
| 7,232,588 | B2 | 6/2007 | Long et al. |
| 7,238,389 | B2 | 7/2007 | Long et al. |
| 7,288,285 | B2 | 10/2007 | Long et al. |
| 7,288,286 | B2 | 10/2007 | Long et al. |
| 7,625,601 | B2 | 12/2009 | Long et al. |
| 7,767,317 | B2 | 8/2010 | Begley et al. |
| 2002/0022151 | A1 | 2/2002 | Ishikawa et al. |
| 2002/0086180 | A1* | 7/2002 | Seo et al. ............. 428/690 |
| 2002/0168544 | A1 | 11/2002 | Fukuoka et al. |
| 2003/0044643 | A1 | 3/2003 | Arakane et al. |
| 2003/0068528 | A1 | 4/2003 | Thompson et al. |
| 2004/0113547 | A1 | 6/2004 | Son et al. |
| 2004/0207318 | A1 | 10/2004 | Lee et al. |
| 2004/0255857 | A1 | 12/2004 | Chow et al. |
| 2005/0067955 | A1 | 3/2005 | Cho et al. |
| 2005/0097955 | A1 | 5/2005 | Berg et al. |
| 2005/0244676 | A1 | 11/2005 | Arakane et al. |
| 2005/0271889 | A1 | 12/2005 | Dolinar |
| 2005/0271899 | A1 | 12/2005 | Brown et al. |
| 2006/0063030 | A1 | 3/2006 | Deaton et al. |
| 2006/0097227 | A1 | 5/2006 | Okajima et al. |
| 2006/0134460 | A1 | 6/2006 | Kondakova et al. |
| 2006/0141287 | A1 | 6/2006 | Klubek et al. |
| 2006/0177576 | A1 | 8/2006 | Long et al. |
| 2006/0204784 | A1 | 9/2006 | Begley et al. |
| 2006/0238110 | A1 | 10/2006 | Shirai et al. |
| 2006/0246315 | A1 | 11/2006 | Begley et al. |
| 2006/0257684 | A1 | 11/2006 | Arakane et al. |
| 2006/0286405 | A1 | 12/2006 | Begley et al. |
| 2007/0063189 | A1 | 3/2007 | Schwalm et al. |
| 2007/0069198 | A1* | 3/2007 | Dotz et al. ............. 257/40 |
| 2007/0092756 | A1 | 4/2007 | Begley et al. |
| 2007/0092759 | A1 | 4/2007 | Begley et al. |
| 2007/0122657 | A1 | 5/2007 | Klubek et al. |
| 2007/0149815 | A1 | 6/2007 | Takada et al. |
| 2007/0164669 | A1 | 7/2007 | Yu et al. |
| 2007/0207347 | A1 | 9/2007 | Begley et al. |
| 2007/0252516 | A1* | 11/2007 | Kondakova et al. ........ 313/504 |
| 2008/0007160 | A1 | 1/2008 | Sado et al. |
| 2009/0108734 | A1 | 4/2009 | Begley et al. |
| 2009/0108735 | A1 | 4/2009 | Begley et al. |
| 2009/0108736 | A1 | 4/2009 | Begley et al. |
| 2009/0110956 | A1 | 4/2009 | Begley et al. |

FOREIGN PATENT DOCUMENTS

| | | |
|---|---|---|
| EP | 0 732 868 | 9/1996 |
| EP | 0 891 121 A1 | 1/1999 |
| EP | 1 009 041 | 6/2000 |
| EP | 1 029 909 A1 | 8/2000 |
| EP | 1 076 368 | 2/2001 |
| EP | 1 097 980 | 5/2001 |
| EP | 1 718 124 A1 | 11/2006 |
| EP | 1 719 748 A2 | 11/2006 |
| JP | 8-333569 | 12/1996 |
| JP | 09-13026 | 1/1997 |
| JP | 2000-53957 | 2/2000 |
| JP | 2001-267080 | 9/2001 |
| JP | 2002-69044 | 3/2002 |
| JP | 2003-105332 | 4/2003 |
| JP | 2003-115387 | 4/2003 |
| JP | 2003-123983 | 4/2003 |
| JP | 2003-138251 | 5/2003 |
| JP | 2004-091444 | 3/2004 |
| JP | 2004-175691 | 6/2004 |
| JP | 2004-311184 | 11/2004 |
| JP | 2005-240008 | 9/2005 |
| JP | 2005-320286 | 11/2005 |
| WO | WO 98/55561 | 12/1998 |
| WO | WO 99/63023 | 12/1999 |
| WO | WO 00/18851 | 4/2000 |
| WO | WO 00/57676 | 9/2000 |
| WO | WO 00/70655 | 11/2000 |
| WO | WO 01/41512 | 6/2001 |
| WO | WO 01/93642 | 12/2001 |
| WO | WO 02/43449 | 5/2002 |
| WO | WO 2004/026870 | 4/2004 |
| WO | WO 2005/033051 A1 * | 4/2005 |
| WO | WO 2006/138075 | 12/2006 |
| WO | WO 2007/072889 | 6/2007 |
| WO | WO 2007/126112 | 11/2007 |
| WO | WO 2008/143796 | 11/2008 |

OTHER PUBLICATIONS

R. Tseng et al., Applied Physics Letters (2006), 88(9), 09351/1-3.

Nonoyama, "Benzo[h]quinolin-10-yl-N Iridium (III) Complexes", Bulletin of the Chemical Society of Japan, vol. 47(3), pp. 767-768, 1974.

Johnson et al., "Luminescent Iridium(I), Rhodium(I), and Platinum(II) Dithiolate Complexes", Journal of American Chemical Society, vol. 105, pp. 1795-1802, 1983.

Wrighton et al., The Nature of the Lowest Excited State in Tricarbonylchloro-1,10-phenanthrolinerhenium(I) and Related Complexes, Journal of the American Chemical Society, vol. 96, No. 4, pp. 998-1003, 1974.

Yam, "Luminescent carbon-rich rhenium(I) complexes", Chem. Commun. pp. 789-796, 2001.

Ma et al., "Electroluminescence from triplet metal-ligand charge-transfer excited state of transition metal complexes", Synthetic Metals 94, pp. 245-248, 1998.

Kido et al., "Electroluminescence in a Terbium Complex", Chem. Lett. pp. 657-660, 1990.

Kido et al., "Organic electroluminescent devices using lanthanide complexes", J. Alloys and Compounds 192, pp. 30-33, 1993.

Kido et al., White-Light-Emitting Organic Electroluminescent Device Using Lanthanide Complexes, Jpn. J. Appl. Phys., vol. 35, pp. L394-L396, 1996.

Kido et al., "Bright red light-emitting organic electroluminescent devices having a europium complex as an emitter", Appl. Phys. Lett., 65 (17), pp. 2124-2126, 1994.

Chen et al., "Recent Developments in Molecular Organic Electroluminescent Materials", Macromol. Symp. 125, pp. 1-48, 1997.

Hung et al., "Recent progress of molecular organic electroluminescent materials and devices", Materials Science and Engineering R39, pp. 143-222, 2002.

Gordon H. Rule and Samuel B. Thompson; Journal of the Chemical Society, (1937), 1761-1763.

Velusamy et al, Synthesis Electroluminescent, 2007, The Royal Chem. Society, Dalton Trans., pp. 3025-3034.

Efficient Blue-Light-Emitting electroluminescent Devices with a Robust fluorophore:7, 8, 1-Triphenylfluoranthene, by Ryan C. Chiechi, et al Adv. mater. 2006, 18, 325-325.

W. Dilthey, I. Ter Horst and W. Schommer; "Journal fuer Praktische Chemie (Leipzig)", 143, (1935), 189-210.

P. Bergmann et al., Chemische Berichte, "Zur Synthese gemischter Hexa-hetaryl-aryl-benzole und ähnlicher Verbindungen", 828-835 (1967).

C. Tang et al., "Electroluminescence of Doped Organic Thin Films", Journal of Applied Physics, 65,3610 (1989).

Stufkens, Comments Inorg. Chem., 13, 359 (1992).

* cited by examiner

OLED DEVICE WITH CERTAIN FLUORANTHENE HOST

CROSS-REFERENCE TO RELATED APPLICATION

U.S. patent application Ser. No. 11/924,629 entitled OLED DEVICE WITH CERTAIN FLUORANTHENE LIGHT-EMITTING DOPANTS filed on Oct. 26, 2007;

U.S. patent application Ser. No. 11/924,631 entitled OLED DEVICE WITH FLUORANTHENE ELECTRON TRANSPORT MATERIALS filed on Oct. 26, 2007;

U.S. patent application Ser. No. 11/924,626 entitled OLED DEVICE WITH CERTAIN FLUORANTHENE HOST filed on Oct. 26, 2007;

U.S. patent application Ser. No. 11/924,624 entitled OLED DEVICE WITH ELECTRON TRANSPORT MATERIAL COMBINATION filed on Oct. 26, 2007; and U.S. patent application Ser. No. 11/924,635 entitled PHOSPHORESCENT OLED DEVICE WITH CERTAIN FLUORANTHENE HOST filed on Oct. 26, 2007.

FIELD OF THE INVENTION

This invention relates to an organic light-emitting diode (OLED) electroluminescent (EL) device having a light-emitting layer including a specific type of fluoranthene host material and an electron injection layer including an organic lithium material.

BACKGROUND OF THE INVENTION

While organic electroluminescent (EL) devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", RCA Review, 30, 322, (1969); and Dresner U.S. Pat. No. 3,710,167, issued Jan. 9, 1973. The organic layers in these devices, usually composed of a polycyclic aromatic hydrocarbon, were very thick (much greater than 1 μm). Consequently, operating voltages were very high, often greater than 100V.

More recent organic EL devices include an organic EL element consisting of extremely thin layers (e.g. <1.0 μm) between the anode and the cathode. Herein, the term "organic EL element" encompasses the layers between the anode and cathode. Reducing the thickness lowered the resistance of the organic layers and has enabled devices that operate at much lower voltage. In a basic two-layer EL device structure, described first in U.S. Pat. No. 4,356,429, one organic layer of the EL element adjacent to the anode is specifically chosen to transport holes, and therefore is referred to as the hole-transporting layer, and the other organic layer is specifically chosen to transport electrons and is referred to as the electron-transporting layer. Recombination of the injected holes and electrons within the organic EL element results in efficient electroluminescence.

There have also been proposed three-layer organic EL devices that contain an organic light-emitting layer (LEL) between the hole-transporting layer and electron-transporting layer, such as that disclosed by C. Tang et al. (J. Applied Physics, Vol. 65, 3610 (1989)). The light-emitting layer commonly consists of a host material doped with a guest material, otherwise known as a dopant. Still further, there has been proposed in U.S. Pat. No. 4,769,292 a four-layer EL element comprising a hole injecting layer (HIL), a hole-transporting layer (HTL), a light-emitting layer (LEL) and an electron-transporting/injecting layer (ETL). These structures have resulted in improved device efficiency.

EL devices in recent years have expanded to include not only single color emitting devices, such as red, green and blue, but also white-devices, devices that emit white light. Efficient white light producing OLED devices are highly desirable in the industry and are considered as a low cost alternative for several applications such as paper-thin light sources, backlights in LCD displays, automotive dome lights, and office lighting. White light producing OLED devices should be bright, efficient, and generally have Commission International d'Eclairage (CIE) chromaticity coordinates of about (0.33, 0.33). In any event, in accordance with this disclosure, white light is that light which is perceived by a user as having a white color.

Since the early inventions, further improvements in device materials have resulted in improved performance in attributes such as color, stability, luminance efficiency and manufacturability, e.g., as disclosed in U.S. Pat. Nos. 5,061,569, 5,409,783, 5,554,450, 5,593,788, 5,683,823, 5,908,581, 5,928,802, 6,020,078, and U.S. Pat. No. 6,208,077, amongst others.

Notwithstanding all of these developments, there are continuing needs for organic EL device components, such as hosts for light-emitting layers and/or electron injecting materials, that will provide even lower device drive voltages and hence lower power consumption, while maintaining high luminance efficiencies and long lifetimes combined with high color purity.

A useful class of electron-transporting materials is that derived from metal chelated oxinoid compounds including chelates of oxine itself, also commonly referred to as 8-quinolinol or 8-hydroxyquinoline. Tris(8-quinolinolato)aluminum (III), also known as Alq or $Alq_3$, and other metal and non-metal oxine chelates are well known in the art as electron-transporting materials. Tang et al., in U.S. Pat. No. 4,769,292 and VanSlyke et al., in U.S. Pat. No. 4,539,507 lower the drive voltage of the EL devices by teaching the use of Alq as an electron transport material in the luminescent layer or luminescent zone. Baldo et al., in U.S. Pat. No. 6,097,147 and Hung et al., in U.S. Pat. No. 6,172,459 teach the use of an organic electron-transporting layer adjacent to the cathode so that when electrons are injected from the cathode into the electron-transporting layer, the electrons traverse both the electron-transporting layer and the light-emitting layer.

Fluoranthene derivatives are well known in the art as being useful as light-emitting compounds; for example, see US20050271899A1, U.S Pat. No. 6,613,454, US20020168544A1, U.S Pat. Nos. 7,183,010B2, 7,175,922B2, EP1718124A1, EP1719748A2, US20060141287A1, JP2005240008 and US20070069198.

In particular, examples of 7,10-diaryl-fluoranthene derivatives as light-emitting compounds have been disclosed in JP2002069044, JP2005320286, US2007/0069198, US2005/0067955, US2006/0246315, U.S. Pat. Nos. 6,803,120, 6,866,947, WO2007/039344 and R. Tseng et al, Applied Physics Letters (2006), 88(9), 09351/1-3. 3,8-Diphenylfluoranthene derivatives are disclosed as light to emitters in US2007/0063189.

US 20020022151A1 describes the use of 7,10-diaryl-fluoranthenes with at least one amino group directly substituted on the fluoranthene ring in light emitting layers as well as hole and electron transporting layers. US2007149815 describes the use of aromatic bis-amines with fluoranthene substitutents. US20060238110A1 and WO2007039344A2 describe the use of polymeric fluoranthene derivatives as blue light-emitting dopants.

The use of organic lithium compounds in an electron-injection layer of an EL device is also known; for example, see US20060286405, US20020086180, US20040207318, U.S. Pat. No. 6,396,209, JP2000053957, WO9963023 and U.S. Pat. No. 6,468,676.

US2005/0244676 discloses the use of a 3-substituted fluoranthene derivatives with annulated rings in a light-emitting layer in combination with organic lithium salts in an electron-injecting layer.

The use of substituted fluoranthenes in an electron-transporting layer has been described in US2006/0257684.

However, these devices do not have all desired EL characteristics in terms of high luminance and stability of the components in combination with low drive voltages.

Notwithstanding all these developments, there remains a need to increase efficiency and operational stability of OLED devices, as well as to provide embodiments with other improved features such as improved white color balance.

SUMMARY OF THE INVENTION

The invention provides an OLED device comprising a cathode, an anode, and having therebetween:

(a) a light emitting layer containing a non-light-emitting fluoranthene compound with a 7,10-diaryl substituted fluoranthene nucleus having no aromatic rings annulated (fused) to the fluoranthene nucleus; and (b) comprising still further an additional layer, containing an organic alkali metal compound, located between the cathode and the electron transporting layer.

In another embodiment, the OLED device also includes an electron-transporting layer comprising a 7,10-diaryl-fluoranthene compound with no aromatic rings annulated to the fluoranthene nucleus, and optionally, may contain an organic lithium compound.

OLED devices of the invention may exhibit high efficiency, operational stability and improved color, and provide embodiments with other improved features such as low drive voltage.

DETAILED DESCRIPTION OF THE INVENTION

Figure 1:
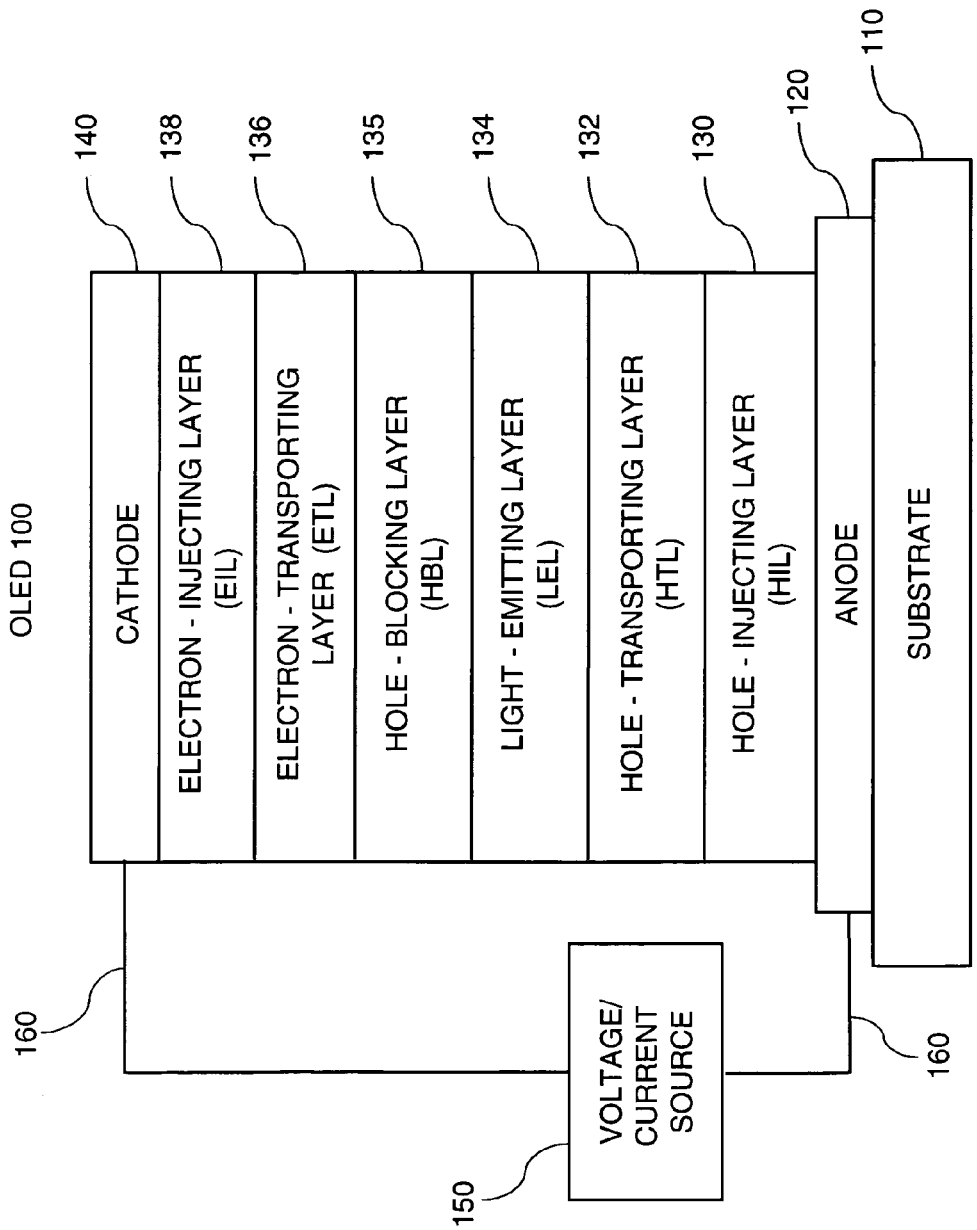
FIG. 1 shows a schematic cross-sectional view of one embodiment of the OLED device of the present invention. It will be understood that FIG. 1 is not to scale since the individual layers are too thin and the thickness differences of various layers are too great to permit depiction to scale.

The invention is generally as described above. An OLED device of the invention is a multilayer electroluminescent device comprising a cathode, an anode, light-emitting layer(s) (LEL), electron-transporting layer(s) (ETL) and electron-injecting layer(s) (EIL) and optionally additional layers such as hole-injecting layer(s), hole-transporting layer(s), exciton-blocking layer(s), spacer layer(s), connecting layer(s) and hole-blocking layer(s).

Without restricting the invention to any particular operating theory, one possible mechanism of light-emission is as follows. When two or more materials are present in a light-emitting layer, they can usually be classified as host and dopant materials. The host material(s) is usually present in larger amount than the dopant(s). The exact roles of the host and the dopant in the process of electroluminescence can vary, and frequently they are not known in detail or with certainty. However, usually the host is responsible for transporting charge (electrons and/or holes), and frequently the recombination occurs between electrons and holes that are both carried by molecules of the host. In any case, the immediate result is typically a host molecule in an excited state. Subsequently, the host molecule transfers its excess energy to a dopant molecule. Now it is the dopant molecule that is excited, and it can radiate its excess energy as luminescent emission in a desired spectral region. To function in this manner, a host material should have good charge-transporting properties for electrons and/or holes. A single material may be used as an electron- and hole transporting host, or a combination of materials may be used wherein one component transports primarily electrons and another component transports primarily holes or a single material may be used to transport only electrons or only holes. In examples where a host carries predominately only electrons or only holes, recombination probably occurs in the region of the interface with a neighboring layer that is capable of predominately transporting the opposite charge (i.e holes or electrons, respectively)

The host is preferably chosen such that every, or almost every recombination event produces an excited state. The host and the dopant should be chosen such that energy transfer from the host to the dopant is efficient, and reverse energy transfer from the dopant to the host is rare. It is usually desirable for substantially all of the luminescence to have the spectrum of the dopant, rather than the host. By 'substantially all', it is meant that more than about 90% of the emitted photons come from the dopant(s). The degree to which the host and the dopant contribute to the emission can be determined by comparing the emission spectrum of the device with the emission spectra of the individual components.

To achieve the proper energy-transfer properties, the host and the dopant are typically selected such that the energy of the excited state of the dopant is lower than that of the host, that the host have some emission in the absence of the dopant, and that the emission spectrum of the host overlap the absorption spectrum of the dopant. The efficiency of emission by the host, however, may be inferior to that by the dopant. The concentration of the dopant may be adjusted to optimize the energy transfer and the efficiency with which the dopant luminesces. In general, the optimum dopant concentration is small compared to that of the host. Too low a dopant concentration generally results in undesired emission from the host, and frequently low efficiency. Too high a dopant concentration typically results in reduced efficiency and undesired spectral shifts, phenomena described as concentration quenching or self-quenching. Suitably, host concentrations in the light-emitting layer should be 50% or greater; more suitably, 75% or greater; or most suitably, 90% or greater with the dopant concentration to be correspondingly, less than 50%; less than 25% and greater than 0.5% with the most desirable range being from 1% to 12%.

Further descriptions of the requirements for host and dopant materials can be found in Chen et al, Macromolecular Symposia (1997), 125, 1-48 and U.S. Pat. No. 7,221,088.

It is known that the same material can be a host or dopant depending on the nature of the other materials present. For example, substituted anthracenes can be used as (1) a non-emittng host with some particular dopants, (2)a light-emitting material when used by itself, or (3) a light-emitting dopant when used with particular hosts; see US20070164669. It is also possible for such a material can be used in additional, non-light-emitting layers such as a hole- or electron-transporting layer.

The LEL of the invention includes a certain type of fluoranthene compound as a non-light-emitting host material and another compound that serves as a light-emitting dopant material. The fluoranthene host material does not emit substantial amounts of light when a potential is applied to the LEL. By substantial, it is meant that the fluoranthene emits no more than about 10% of the total light from that layer. There may be one or more other host materials additionally present in the LEL and the total amount of all hosts present should comprise 50% or more of the total volume of all of the materials in the LEL. It is preferred when the fluoranthene of the invention is used as a co-host together with another host material, that the fluoranthene co-host compose at least 2% of the total amount of materials in the LEL, or more preferably, at least 10%.

The light-emitting compound (commonly referred to as a dopant) is present at less than 50% of the total volume of all materials in the LEL, preferably less than 25% and greater than 0.5% with the most desirable range being from 1% to 12%. There may more than one light-emitting materials that emit the same or different colors of light in the LEL The fluoranthene compounds of the invention are those other than ones where the fluoranthene nucleus contains annulated rings. They are polycyclic aromatic hydrocarbons and contain no heteroatoms as part of the ring system of the nucleus. The fluoranthene nucleus contains only 4 annulated rings whose numbering sequence is shown below:

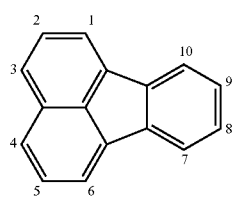 [SMILES: c1ccc2c(c1)-c1cccc3cccc-2c13]

The fluoranthenes of the invention contain no additional annulated rings to the above nucleus. Annulated rings are those rings that share a common ring bond between any two carbon atoms of the fluoranthene nucleus.

Suitably, the 7,10-diaryl-fluoranthene compounds of the invention are according to Formula (I):

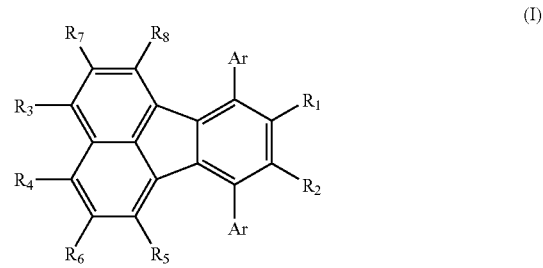

wherein:
each Ar is an aromatic ring containing 6 to 24 carbon atoms and can be the same or different; and $R_1$-$R_8$ are individually selected from hydrogen and aromatic rings containing 6 to 24 carbon atoms with the proviso that no two adjacent $R_1$-$R_8$ substituents can form an annulated or fused aromatic ring system.

In formula (I), the Ar group(s) can be heterocyclic but preferred are carbocyclic groups. The Ar group(s) cannot be fused with the floranthene nucleus and are connected only by one single bond. Preferred Ar groups are phenyl or napthyl with phenyl being particularly preferred. Compounds where the Ar groups are the same are also desirable.

More preferred compounds of the invention are according to Formula (II):

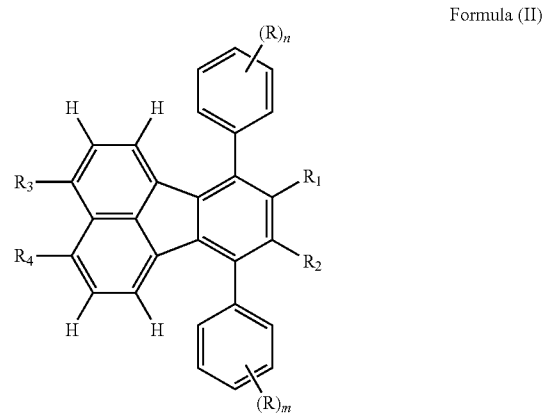

wherein
$R_1$, $R_2$, $R_3$ and $R_4$ are independently hydrogen or an aromatic group containing 6 to 24 carbon atoms with the proviso that any adjacent $R_1$-$R_4$ is not part of an annulated aromatic ring system;

R is hydrogen or an optional substituent; and n and m are independently 1-5.

Most preferred fluoranthenes are according to Formula (III-a) or (III-b):

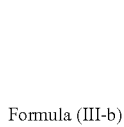

Formula (III-a)

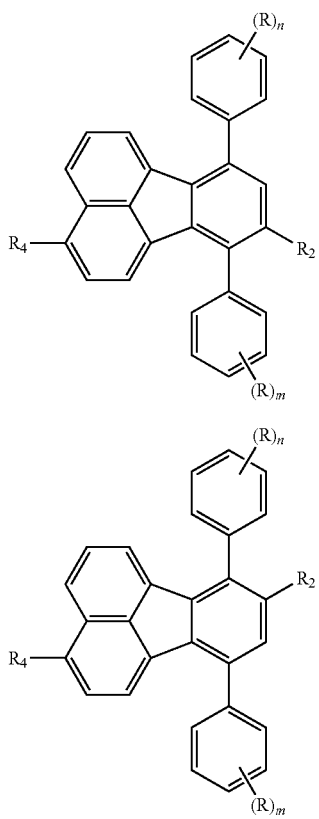

Formula (III-b)

wherein:
R$_2$ and R$_4$ are independently hydrogen or an aromatic group containing 6 to 24 carbon atoms with the proviso that R$_2$ and R$_4$ cannot both be hydrogen nor can R$_2$ be joined with R to form a ring; and
R is hydrogen or an optional substituent; and
n and m are independently 1-5.

In Formulas (II) and (III), the most preferred R$_1$, R$_2$, R$_3$ and R$_4$ groups are phenyl or napthyl, which may be further substituted. A particularly preferred substituted phenyl group is biphenyl. Biphenyl can be ortho(o), meta(m) or para(p) substituted biphenyl, with p-biphenyl being particularly preferred. Other aromatic ring systems such as anthracene, phenanthrene, phenanthroline and perylene are also suitable as these substituents. Typically, the R substituent(s) are hydrogen but may be any suitable group chosen to modify the molecular properties. It is also contemplated that the fluoranthene of the invention can consist of more than one separate fluoranthene nucleus; that is, two or more fluoranthene groups can be linked through a single bond so that they are not annulated together.

However, the fluoranthene derivatives used in the invention are not polymeric; that is, have multiple fluoranthene groups covalently attached to a polymeric backbone or where the fluoranthene nucleus is directly part of the polymeric chain. The fluoranthrenes of the invention are small molecules with molecular weights typically below 1500, preferably below 1000.

In addition, the fluoranthene compounds used in the invention cannot have any amino substitutents attached directly to the fluoranthene nucleus. Thus, none of R$_1$-R$_8$ in Formula (I), (II) or (III) can be an amino group such as diarylamine.

However, it is possible that the aromatic rings containing 6 to 24 carbon atoms of R$_1$-R$_8$ may be further substituted with amino groups.

The fluoranthene compounds used in the invention cannot have additional aromatic rings annulated to either the phenyl or napthyl rings of the fluoranthene ring system. Fluoranthenes with additional annulated ring systems are not part of this invention. Four specific examples of compounds containing a fluoranthene nucleus with annulated ring systems that are excluded are:

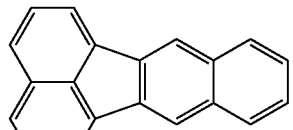

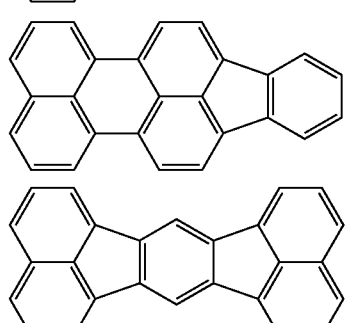

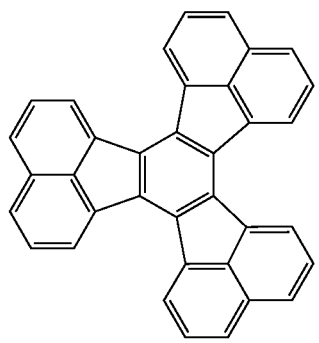

Specific examples of fluoranthene light-emitting materials of the invention are as follows:

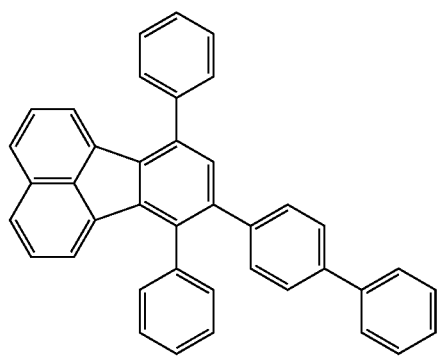

ETM1

-continued
ETM2
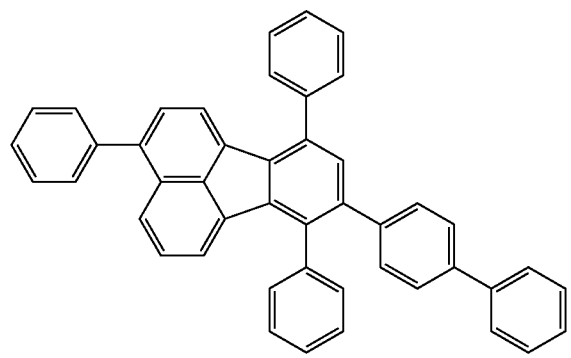
ETM6
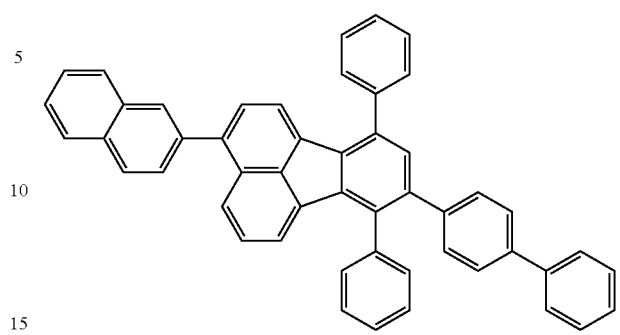
ETM3
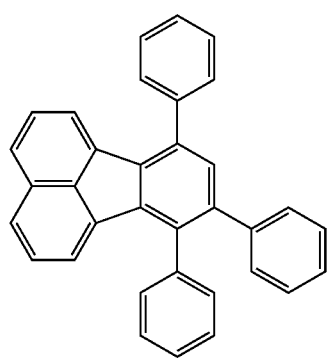
ETM7
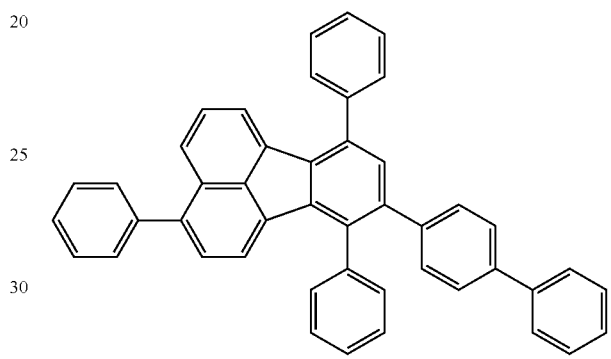
ETM4
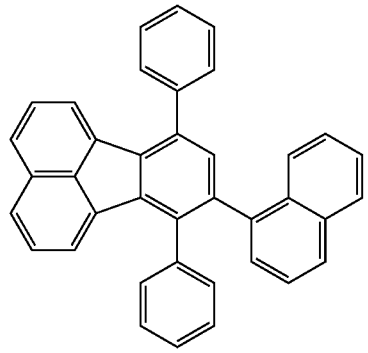
ETM8
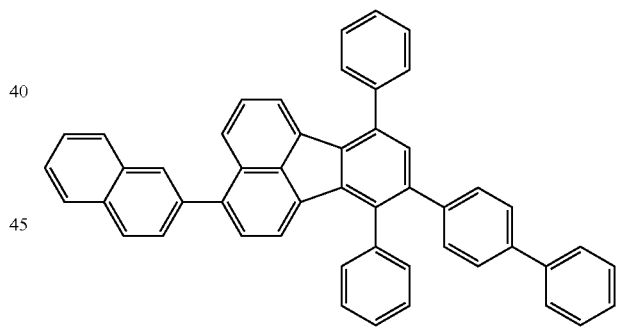
ETM5
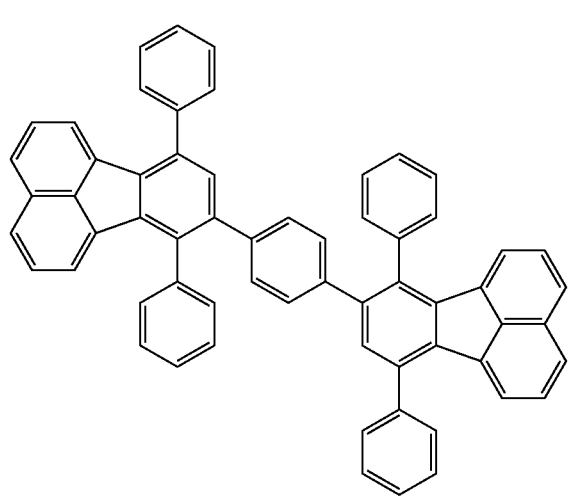
ETM9
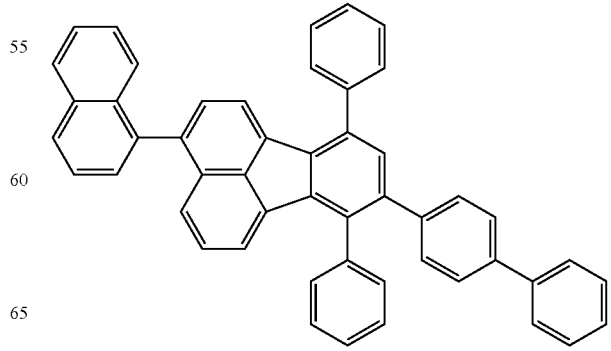

ETM10
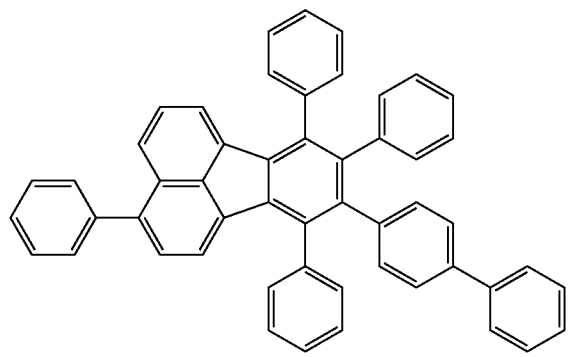
ETM11
ETM12
ETM13
ETM14
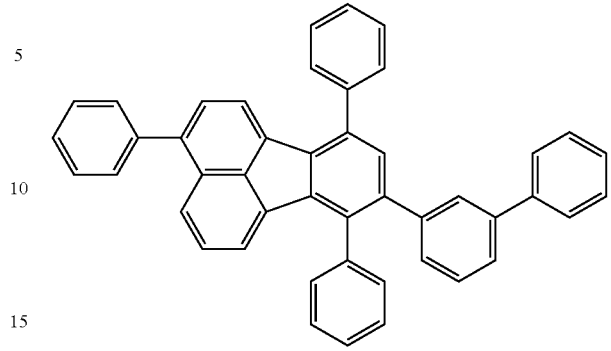
ETM15
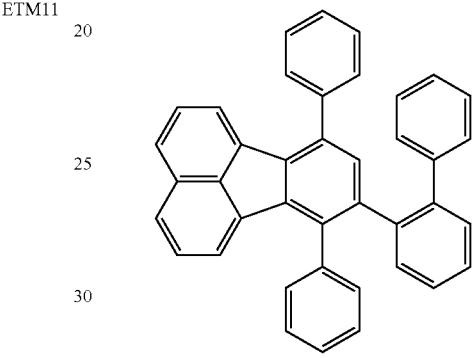
ETM16
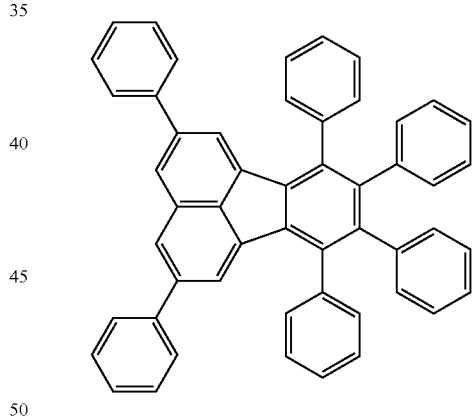
ETM17
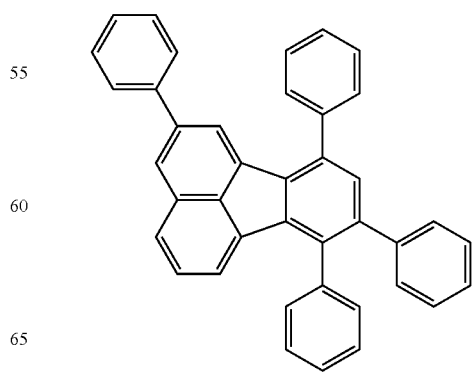

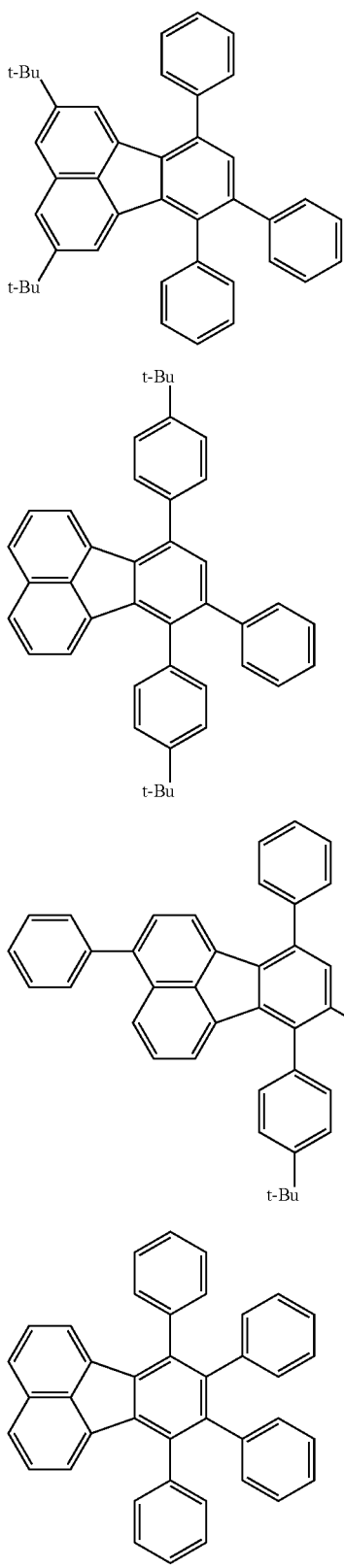

ETM18

ETM19

ETM20

ETM21

The light-emitting layer containing the fluoranthene derivative can emit in any color or combination of colors of light, although blue, yellow and red are preferred with blue being the most preferred. When referring to the color of light emitter, it should be understood that lesser amounts of different color of light may be emitted as well. For example, blue light-emission would refer to a layer where blue light predominates but may emit smaller amounts of green or red as well. The OLED device containing the invention may be a single color or may emit white light.

The invention additionally requires a layer, located between the cathode and the electron-transporting layer that contains an organic alkali metal compound. This layer is typically referred to as an electron-injection layer (EIL). Such layers are commonly located directly adjacent to the cathode and assist in the efficient transfer of electrons towards the light-emitting layer. A common partial layer order is LEL|ETL|EEL| cathode. The ETL and EIL may be split into multiple sublayers. There may be intermediate layers between any of these 3 interfaces; for example, a thin layer of LiF between the cathode and the EIL. The organic alkali metal compounds may also be present in the ETL as well as the EIL.

The EIL may be composed only of a single organic alkali metal compound or may be a mixture of 2 or more organic alkali metal compounds. In addition to the alkali metal compounds, the EL may also contain one or more polycyclic aromatic hydrocarbons. The % volume ratio of organic alkali metal compound to additional material can be anywhere from 1% to 99%, more suitably at least 10% and typically, at least 30%. The thickness of the EIL can be 0.1 nm to 20 nm in thickness, but preferably 0.4 nm to 10 nm, and more preferable from 1 nm to 8 nm.

The alkali metal used in the compounds of the invention belongs to Group 1 of the periodic table. Of these, lithium is highly preferred.

Organic lithium compounds (electron injection material or EIM) useful in the invention are according to Formula (I):

$(Li^+)_m(Q)_n$     Formula (IV)

wherein:
Q is an anionic organic ligand; and
m and n are independently selected integers selected to provide a neutral charge on the complex.

The anionic organic ligand Q is most suitably monoanionic and contains at least one ionizable site consisting of oxygen, nitrogen or carbon. In the case of enolates or other tautomeric systems containing oxygen, it will be considered and drawn with the lithium bonded to the oxygen although the lithium may in fact can be bonded elsewhere to form a chelate. It is also desirable that the ligand contains at least one nitrogen atom that can form a coordinate or dative bond with the lithium. The integers m and n can be greater than 1 reflecting a known propensity for some organic lithium compounds to form cluster complexes.

In another embodiment, Formula (V) represents the EIM.

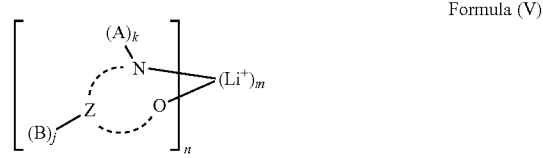

Formula (V)

wherein:
Z and the dashed arc represent two to four atoms and the bonds necessary to complete a 5- to 7-membered ring with the lithium cation;

each A represents hydrogen or a substituent and each B represents hydrogen or an independently selected substituent on the Z atoms, provided that two or more substituents may combine to form a fused ring or a fused ring system; and j is 0-3 and k is 1 or 2; and m and n are independently selected integers selected to provide a neutral charge on the complex.

Of compounds of Formula (V), it is most desirable that the A and B substituents together form an additional ring system. This additional ring system may further contain additional heteroatoms to form a multidentate ligand with coordinate or dative bonding to the lithium. Desirable heteroatoms are nitrogen or oxygen.

In Formula (V), it is preferred that the oxygen shown is part of a hydroxyl, carboxy or keto group. Examples of suitable nitrogen ligands are 8-hydroxyquinoline, 2-hydroxymethylpyridine, pipecolinic acid or 2-pyridinecarboxylic acid.

Specific examples of electron injecting materials of the invention are as follows:

EIM1

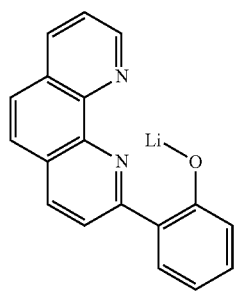

EIM2

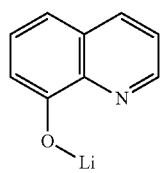

EIM3

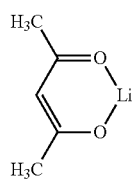

EIM4

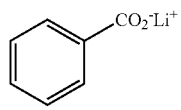

EIM5

EIM7

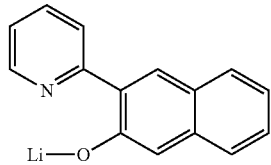

EIM8

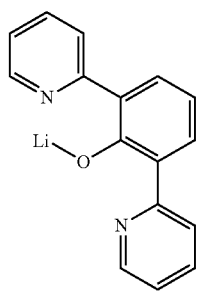

EIM9

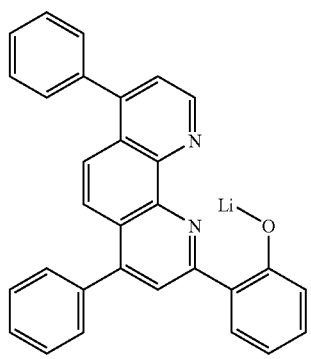

EIM10

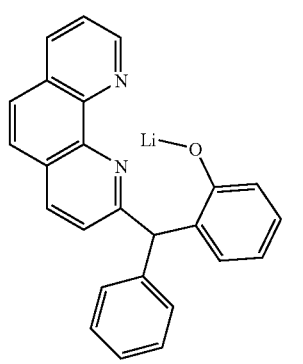

EIM11

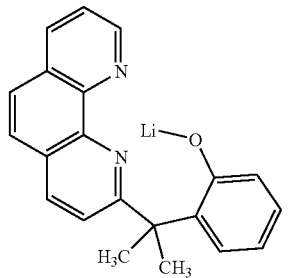

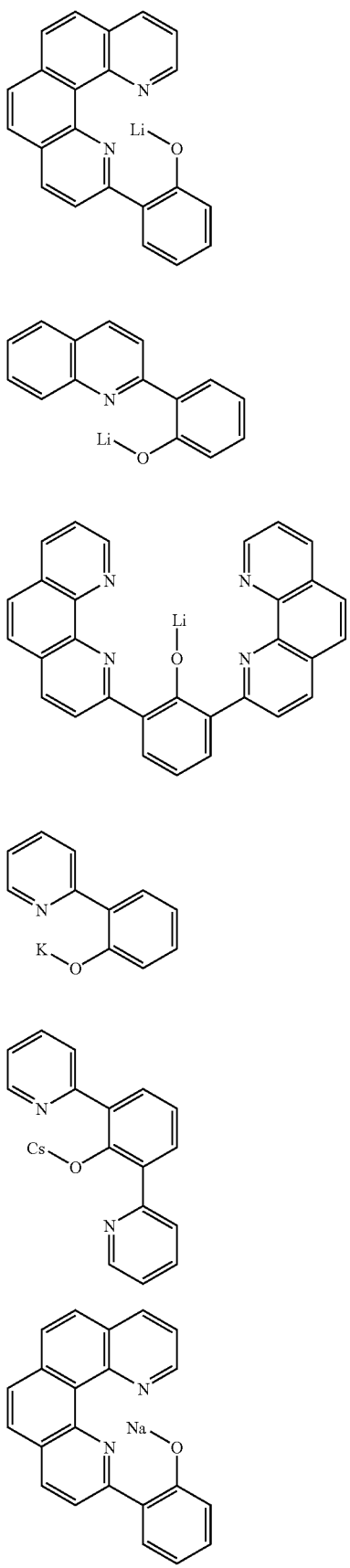

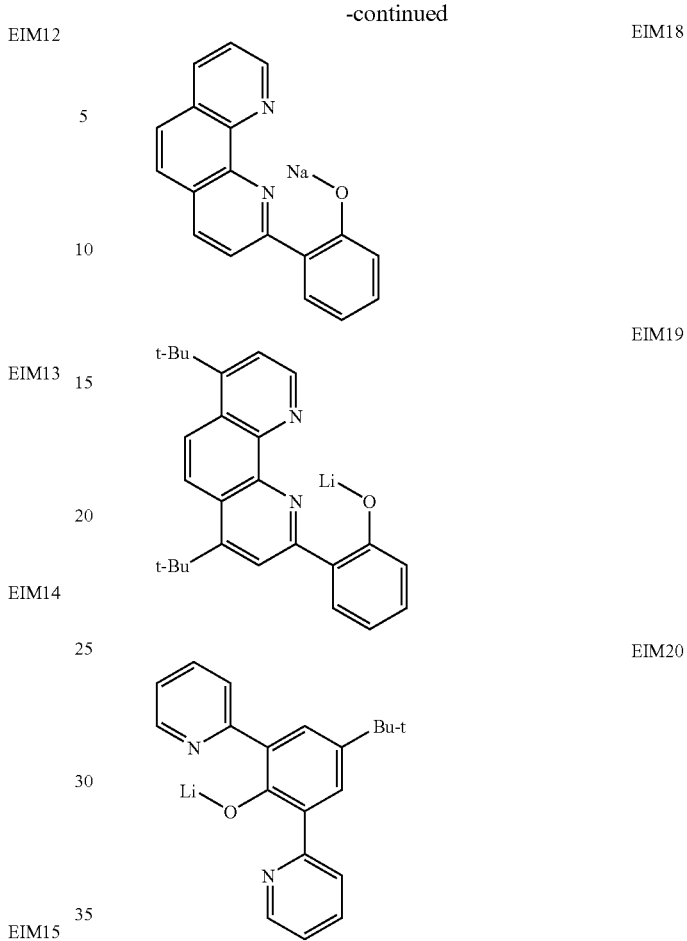

FIG. 1 shows one embodiment of the invention in which light-emitting layers, electron-transporting and electron-injecting layers are present. The fluoranthene compound of the invention is located in the light-emitting layer (LEL, 134). An optional hole-blocking layer (HBL, 135) is shown between the light-emitting layer and the electron-transporting layer. The figure also shows an optional hole-injecting layer (HIL, 130). In this embodiment, the organic lithium compound is contained in the electron-injecting layer (EIL, 138) and serves as the said additional layer. In another embodiment, there is no hole-blocking layer (HBL, 135) located between the ETL and the LEL. In yet other embodiments, there may be more than one hole-injecting, electron-injecting and electron-transporting layers.

Examples of preferred combinations of the invention are those wherein the fluoranthene compound is selected from ETM1, ETM2, ETM3, ETM6, ETM9 and ETM11 and the organic lithium compound is selected from EIM1, EIM2 and EIM3.

The LEL containing the fluoranthene host and the light-emitting compound can produce any color of light. In one embodiment, it is preferred that the LEL emits predominately blue light. In this case, if another additional light-emitting material is present in the same LEL, it is preferred that it emits a colored light other than blue light. The relative amount of any additional light-emitting material may be adjusted so that the entire LEL produces predominately blue light with smaller amounts of light of another color, adjusted so that the LEL produces roughly equivalent of blue and other colors of light such to produce a white light, or adjusted so that the amounts of the other colors of light are greater than the blue light.

The light-emitting materials used with the fluoranthene host may be fluorescent or phosphorescent. While the light-emitting compound is present in the LEL at less than 50% by volume, it is preferred that it is present at less than 25% and greater than 0.5% with the most desirable range being from 1% to 12%.

The LEL containing the fluoranthene may also contain at least one additional host material. Any material known to be a suitable host for a light-emitting layer can be used. It may have hole-transporting properties, electron-transporting properties or possess the ability to do both. Hosts known for being useful with a fluorescent dopant (for examples, see the discussion below concerning fluorescent LELs) are preferred, particularly those with electron-transporting properties. Hosts derived from polycyclic aromatic hydrocarbons are particularly useful with those derived from anthracene being the most useful.

In another embodiment, the OLED device also includes an electron-transporting layer comprising a 7,10-diaryl-fluoranthene compound with no annulated aromatic rings and optionally, may contain an organic lithium compound. The fluoranthene host materials according to this invention have excellent electron-transporting properties that makes them very suitable for use in electron-transporting layers. Suitable fluoranthenes for use in an ETL are those according to Formulae (I), (II) and (III). In an ETL, they may be the sole material present in the layer or may be mixed with additional materials. In particular, it is desirable to include both the fluoranthenes and EIMs of this invention together in an ETL. Suitable EIMs for mixing in the ETL are those according to Formula (IV) or more preferably, those according to Formula (V).

In one suitable embodiment the EL device includes a means for emitting white light, which may include complimentary emitters, a white emitter, or a filtering means. The device may also include combinations of fluorescent emitting materials and phosphorescent emitting materials (sometimes referred to as hybrid OLED devices). To produce a white emitting device, ideally the hybrid fluorescent/phosphorescent device would comprise a blue fluorescent emitter and proper proportions of a green and red phosphorescent emitter, or other color combinations suitable to make white emission. However, hybrid devices having non-white emission may also be useful by themselves. Hybrid fluorescent/phosphorescent elements having non-white emission may also be combined with additional phosphorescent elements in series in a stacked OLED. For example, white emission may be produced by one or more hybrid blue fluorescent/red phosphorescent elements stacked in series with a green phosphorescent element using p/n junction connectors as disclosed in Tang et al U.S. Pat. No. 6,936,961B2. This invention maybe used in so-called stacked device architecture, for example, as taught in U.S. Pat. No. 5,703,436 and U.S. Pat. No. 6,337,492.

In one desirable embodiment the EL device is part of a display device. In another suitable embodiment the EL device is part of an area lighting device.

The EL device of the invention is useful in any device where stable light emission is desired such as a lamp or a component in a static or motion imaging device, such as a television, cell phone, DVD player, or computer monitor.

As used herein and throughout this application, the term carbocyclic and heterocyclic rings or groups are generally as defined by the *Grant & Hackh's Chemical Dictionary*, Fifth Edition, McGraw-Hill Book Company. A carbocyclic ring is any aromatic or non-aromatic ring system containing only carbon atoms and a heterocyclic ring is any aromatic or non-aromatic ring system containing both carbon and non-carbon atoms such as nitrogen (N), oxygen (O), sulfur (S), phosphorous (P), silicon (Si), gallium (Ga), boron (B), beryllium (Be), indium (In), aluminum (Al), and other elements found in the periodic table useful in forming ring systems. For the purpose of this invention, also included in the definition of a heterocyclic ring are those rings that include coordinate bonds. The definition of a coordinate or dative bond can be found in *Grant & Hackh's Chemical Dictionary*, pages 91 and 153. In essence, a coordinate bond is formed when electron rich atoms such as O or N, donate a pair of electrons to electron deficient atoms or ions such as aluminum, boron or alkali metal ions such as $Li^+$, $Na^+$, $K^+$ and $Cs^+$. One such example is found in tris(8-quinolinolato)aluminum(III), also referred to as Alq, wherein the nitrogen on the quinoline moiety donates its lone pair of electrons to the aluminum atom thus forming the heterocycle and hence providing Alq with a total of 3 fused rings. The definition of a ligand, including a multidentate ligand, can be found in *Grant & Hackh's Chemical Dictionary*, pages 337 and 176, respectively.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for device utility. Suitably, a substituent group may be halogen or may be bonded to the remainder of the molecule by an atom of carbon, silicon, oxygen, nitrogen, phosphorous, sulfur, selenium, or boron. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy)propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy, aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylanino, p-dodecylphenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N- dipropylsulfamoylamino, and hexadecylsulfonamido; sulfamoyl, such as N-methylsulfamoyl, N-ethylsulfamoyl, N,N-propylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen, sulfur, phosphorous, or boron. Such as 2-furyl, 2-thienyl, 2-benzimidazolyloxy or 2-benzothiazolyl; quaternary ammonium, such as triethylammonium; quaternary phosphonium, such as triphenylphosphonium; and silyloxy, such as trimethylsilyloxy.

If desired, the substituents may themselves be further substituted one or more times with the described substituent groups. The particular substituents used may be selected by those skilled in the art to attain desirable properties for a specific application and can include, for example, electron-withdrawing groups, electron-donating groups, and steric groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The following is the description of the layer structure, material selection, and fabrication process for OLED devices.

General OLED Device Architecture

The present invention can be employed in many OLED configurations using small molecule materials, oligomeric materials, polymeric materials, or combinations thereof. These include from very simple structures having a single anode and cathode to more complex devices, such as passive matrix displays having orthogonal arrays of anodes and cathodes to form pixels, and active-matrix displays where each pixel is controlled independently, for example, with thin film transistors (TFTs). There are numerous configurations of the organic layers wherein the present invention is successfully practiced. For this invention, essential requirements are a cathode, an anode, a LEL, an ETL and a HIL.

One embodiment according to the present invention and especially useful for a small molecule device is shown in FIG. 1. OLED 100 contains a substrate 110, an anode 120, a hole-injecting layer 130, a hole-transporting layer 132, a light-emitting layer 134, a hole-blocking layer 135, an electron-transporting layer 136, an electron-injecting layer 138 and a cathode 140. In some other embodiments, there are optional spacer layers on either side of the LEL. These spacer layers do not typically contain light emissive materials. All of these layer types will be described in detail below. Note that the substrate may alternatively be located adjacent to the cathode, or the substrate may actually constitute the anode or cathode. Also, the total combined thickness of the organic layers is preferably less than 500 nm.

The anode and cathode of the OLED are connected to a voltage/current source 150, through electrical conductors 160. Applying a potential between the anode and cathode such that the anode is at a more positive potential than the cathode operates the OLED. Holes are injected into the organic EL element from the anode. Enhanced device stability can sometimes be achieved when the OLED is operated in an AC mode where, for some time period in cycle, the potential bias is reversed and no current flows. An example of an AC driven OLED is described in U.S. Pat. No. 5,552,678.

Anode

When the desired EL emission is viewed through the anode, anode 120 should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode 120. For applications where EL emission is viewed only through the cathode 140, the transmissive characteristics of the anode 120 are immaterial and any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize short circuits or enhance reflectivity.

Hole Injection Layer

Although it is not always necessary, it is often useful to provide an HIL in the OLEDs. HIL 130 in the OLEDs can serve to facilitate hole injection from the anode into the HTL, thereby reducing the drive voltage of the OLEDs. Suitable materials for use in HIL 130 include, but are not limited to, porphyrinic compounds as described in U.S. Pat. No. 4,720,432 and some aromatic amines, for example, 4,4',4"-tris[(3-ethylphenyl)phenylamino]triphenylamine (m-TDATA). Alternative hole-injecting materials reportedly useful in OLEDs are described in EP 0 891 121 A1 and EP 1 029 909 A1. Aromatic tertiary amines discussed below can also be useful as hole-injecting materials. Other useful hole-injecting materials such as dipyrazino[2,3-f:2',3'-h]quinoxalinehexacarbonitrile are described in U.S. Patent Application Publication 2004/0113547 A1 and U.S. Pat. No. 6,720,573. In addition, a p-type doped organic layer is also useful for the HIL as described in U.S. Pat. No. 6,423,429. The term "p-type doped organic layer" means that this layer has semiconducting properties after doping, and the electrical current through this layer is substantially carried by the holes. The conductivity is provided by the formation of a charge-transfer complex as a result of hole transfer from the dopant to the host material.

The thickness of the HIL 130 is in the range of from 0.1 nm to 200 nm, preferably, in the range of from 0.5 nm to 150 nm.

Hole Transport Layer

The HTL 132 contains at least one hole-transporting material such as an aromatic tertiary amine, where the latter is understood to be a compound containing at least one trivalent nitrogen atom that is bonded only to carbon atoms, at least one of which is a member of an aromatic ring. In one form the aromatic tertiary amine is an arylamine, such as a monoarylamine, diarylamine, triarylamine, or a polymeric arylamine. Exemplary monomeric triarylamines are illustrated by Klupfel et al. U.S. Pat. No. 3,180,730. Other suitable triarylamines substituted with one or more vinyl radicals or at least one active hydrogen-containing group are disclosed by Brantley, et al. in U.S. Pat. Nos. 3,567,450 and 3,658,520.

A more preferred class of aromatic tertiary amines are those which include at least two aromatic tertiary amine moieties as described in U.S. Pat. Nos. 4,720,432 and 5,061,569. Such compounds include those represented by structural Formula (A)

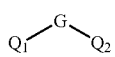

(A)

wherein:
$Q_1$ and $Q_2$ are independently selected aromatic tertiary amine moieties; and
G is a linking group such as an arylene, cycloalkylene, or alkylene group of a carbon to carbon bond.

In one embodiment, at least one of $Q_1$ or $Q_2$ contains a polycyclic fused ring structure, e.g., a naphthalene. When G is an aryl group, it is conveniently a phenylene, biphenylene, or naphthalene moiety.

A useful class of triarylamines satisfying structural Formula A and containing two triarylamine moieties is represented by structural Formula (B)

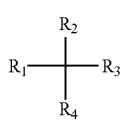

(B)

wherein:
$R_1$ and $R_2$ each independently represents a hydrogen atom, an aryl group, or an alkyl group or $R_1$ and $R_2$ together represent the atoms completing a cycloalkyl group; and
$R_3$ and $R_4$ each independently represents an aryl group, which is in turn substituted with a diaryl substituted amino group, as indicated by structural Formula (C)

(C)

wherein:
$R_5$ and $R_6$ are independently selected aryl groups. In one embodiment, at least one of $R_5$ or $R_6$ contains a polycyclic fused ring structure, e.g., a naphthalene.

Another class of aromatic tertiary amines are the tetraaryldiamines. Desirable tetraaryldiamines include two diarylamino groups, such as indicated by Formula (C), linked through an arylene group. Useful tetraaryldiamines include those represented by Formula (D)

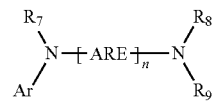

(D)

wherein:
each ARE is an independently selected arylene group, such as a phenylene or anthracene moiety
n is an integer of from 1 to 4; and
Ar, $R_7$, $R_8$, and $R_9$ are independently selected aryl groups. In a typical embodiment, at least one of Ar, $R_7$, $R_8$, and $R_9$ is a polycyclic fused ring structure, e.g., a naphthalene.

Another class of the hole-transporting material comprises a material of formula (E):

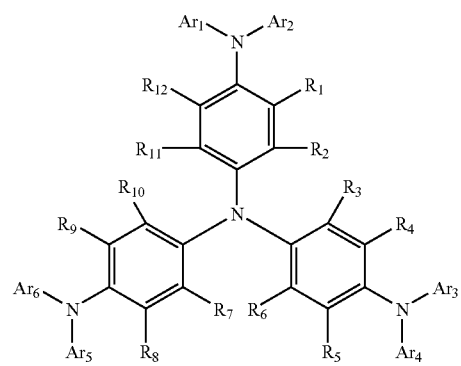

(E)

In formula (E), $Ar_1$-$Ar_6$ independently represent aromatic groups, for example, phenyl groups or tolyl groups;
$R_1$-$R_{12}$ independently represent hydrogen or independently selected substituent, for example an alkyl group containing from 1 to 4 carbon atoms, an aryl group, a substituted aryl group.

The various alkyl, alkylene, aryl, and arylene moieties of the foregoing structural Formulae (A), (B), (C), (D), and (E) can each in turn be substituted. Typical substituents include alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms, e.g. cyclopentyl, cyclohexyl, and cycloheptyl ring structures. The aryl and arylene moieties are typically phenyl and phenylene moieties.

The HTL is formed of a single or a mixture of aromatic tertiary amine compounds. Specifically, one can employ a triarylamine, such as a triarylamine satisfying the Formula (B), in combination with a tetraaryldiamine, such as indicated by Formula (D). When a triarylamine is employed in combination with a tetraaryldiamine, the latter is positioned as a layer interposed between the triarylamine and the electron injecting and transporting layer. Aromatic tertiary amines are useful as hole-injecting materials also. Illustrative of useful aromatic tertiary amines are the following:

- 1,1-bis(4-di-p-tolylaminophenyl)cyclohexane;
- 1,1-bis(4-di-p-tolylaminophenyl)-4-phenylcyclohexane;
- 1,5-bis[N-(1-naphthyl)-N-phenylamino]naphthalene;
- 2,6-bis(di-p-tolylamino)naphthalene;
- 2,6-bis[di-(1-naphthyl)amino]naphthalene;
- 2,6-bis[N-(1-naphthyl)-N-(2-naphthyl)amino]naphthalene;
- 2,6-bis[N,N-di(2-naphthyl)amine]fluorene;
- 4-(di-p-tolylamino)-4'-[4(di-p-tolylamino)-styryl]stilbene;
- 4,4'-bis(diphenylamino)quadriphenyl;
- 4,4"-bis[N-(1-anthryl)-N-phenylamino]-p-terphenyl;
- 4,4'-bis[N-(1-coronenyl)-N-phenylamino]biphenyl;
- 4,4'-bis[N-(1-naphthyl)-N-phenylamino]biphenyl (NPB);
- 4,4'-bis[N-(1-naphthyl)-N-(2-naphthyl)amino]biphenyl (TNB);
- 4,4"-bis[N-(1-naphthyl)-N-phenylamino]p-terphenyl;
- 4,4'-bis[N-(2-naphthacenyl)-N-phenylamino]biphenyl;
- 4,4'-bis[N-(2-naphthyl)-N-phenylamino]biphenyl;
- 4,4'-bis[N-(2-perylenyl)-N-phenylamino]biphenyl;
- 4,4'-bis[N-(2-phenanthryl)-N-phenylamino]biphenyl;
- 4,4'-bis[N-(2-pyrenyl)-N-phenylamino]biphenyl;
- 4,4'-bis[N-(3-acenaphthenyl)-N-phenylamino]biphenyl;
- 4,4'-bis[N-(3-methylphenyl)-N-phenylamino]biphenyl (TPD);
- 4,4'-bis[N-(8-fluoranthenyl)-N-phenylamino]biphenyl;
- 4,4'-bis[N-(9-anthryl)-N-phenylamino]biphenyl;
- 4,4'-bis{N-phenyl-N-[4-(1-naphthyl)-phenyl]amino}biphenyl;
- 4,4'-bis[N-phenyl-N-(2-pyrenyl)amino]biphenyl;
- 4,4',4"-tris[(3-methylphenyl)phenylamino]triphenylamine (m-TDATA);
- Bis(4-dimethylamino-2-methylphenyl)-phenylmethane;
- N-phenylcabazole;
- N,N'-bis[4-([1,1'-biphenyl]-4-ylphenylamino)phenyl]-N,N'-di-1-naphthalenyl-[1,1'-biphenyl]-4,4'-diamine;
- N,N'-bis[4-(di-1-naphthalenylamino)phenyl]-N,N'-di-1-naphthalenyl-[1,1'-biphenyl]-4,4'-diamine;
- N,N'-bis[4-[(3-methylphenyl)phenylamino]phenyl]-N,N'-diphenyl-[1,1'-biphenyl]-4,4'-diamine;
- N,N-bis[4-(diphenylamino)phenyl]-N',N'-diphenyl-[1,1'-biphenyl]-4,4'-diamine;
- N,N'-di-1-naphthalenyl-N,N'-bis[4-(1-naphthalenylphenylamino)phenyl]-[1,1'-biphenyl]-4,4'-diamine;
- N,N'-di-1-naphthalenyl-N,N'-bis[4-(2-naphthalenylphenylamino)phenyl]-[1,1'-biphenyl]-4,4'-diamine;
- N,N,N-tri(p-tolyl)amine;
- N,N,N',N'-tetra-p-tolyl-4,4'-diaminobiphenyl;
- N,N,N',N'-tetraphenyl-4,4'-diaminobiphenyl;
- N,N,N',N'-tetra-1-naphthyl-4,4'-diaminobiphenyl;
- N,N,N',N'-tetra-2-naphthyl-4,4'-diaminobiphenyl; and
- N,N,N',N'-tetra(2-naphthyl)-4,4"-diamino-p-terphenyl.

Another class of useful hole-transporting materials includes polycyclic aromatic compounds as described in EP 1 009 041. Tertiary aromatic amines with more than two amine groups can be used including oligomeric materials. In addition, polymeric hole-transporting materials are used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS.

The thickness of the HTL 132 is in the range of from 5 nm to 200 nm, preferably, in the range of from 10 nm to 150 nm.

Exciton Blocking Layer (EBL)

An optional exciton- or electron-blocking layer may be present between the HTL and the LEL (not shown in FIG. 1). Some suitable examples of such blocking layers are described in U.S. App 20060134460 A1.

Light Emitting Layer

As more fully described in U.S. Pat. Nos. 4,769,292 and 5,935,721, the light-emitting layer(s) (LEL) 134 of the organic EL element shown in FIG. 1 comprises a luminescent, fluorescent or phosphorescent material where electroluminescence is produced as a result of electron-hole pair recombination in this region. The light-emitting layer can be comprised of a single material, but more commonly consists of non-electroluminescent compounds (generally referred to as the host) doped with an electroluminescent or light-emitting guest compound (generally referred to as the dopant) or compounds where light emission comes primarily from the electroluminescent compound and can be of any color. In this invention, the host is a fluoranthene derivative. The non-electroluminescent compounds can be coated as 0.01 to less than 50% by volume into the non-electroluminescent component material, but typically coated as 0.01 to 30% and more typically coated as 0.01 to 15% into the non-electroluminescent component. In this invention, the most desirable range for the light-emitting compound is 1 to 12%. The thickness of the LEL can be any suitable thickness. It can be in the range of from 0.1 mm to 100 mm.

A LEL can be a single light-emitting layer or a light-emitting zone composed of a series of individual light-emitting sublayers. These sublayers can emit the same or different colors of light.

An important relationship for choosing a dye as a electroluminescent component is a comparison of the bandgap potential which is defined as the energy difference between the highest occupied molecular orbital and the lowest unoccupied molecular orbital of the molecule. For efficient energy transfer from the non-electroluminescent compound to the electroluminescent compound molecule, a necessary condition is that the band gap of the electroluminescent compound is smaller than that of the non-electroluminescent compound or compounds. Thus, the selection of an appropriate host material is based on its electronic characteristics relative to the electronic characteristics of the electroluminescent compound, which itself is chosen for the nature and efficiency of the light emitted. As described below, fluorescent and phosphorescent dopants typically have different electronic characteristics so that the most appropriate hosts for each may be different. However in some cases, the same host material can be useful for either type of dopant.

Non-electroluminescent compounds and emitting molecules known to be of use include, but are not limited to, those disclosed in U.S. Pat. Nos. 4,768,292, 5,141,671, 5,150,006, 5,151,629, 5,405,709, 5,484,922, 5,593,788, 5,645,948, 5,683,823, 5,755,999, 5,928,802, 5,935,720, 5,935,721, and 6,020,078.

a) Phosphorescent light emitting layers

Suitable hosts for phosphorescent LELs should be selected so that transfer of a triplet exciton can occur efficiently from the host to the phosphorescent dopant(s) but cannot occur efficiently from the phosphorescent dopant(s) to the host. Therefore, it is highly desirable that the triplet energy of the host be higher than the triplet energies of phosphorescent dopant. Generally speaking, a large triplet energy implies a large optical band gap. However, the band gap of the host should not be chosen so large as to cause an unacceptable barrier to injection of holes into the fluorescent blue LEL and an unacceptable increase in the drive voltage of the OLED. The host in a phosphorescent LEL may include any of the aforementioned hole-transporting material used for the HTL 132, as long as it has a triplet energy higher than that of the phosphorescent dopant in the layer. The host used in a phosphorescent LEL can be the same as or different from the hole-transporting material used in the HTL 132. In some cases, the host in the phosphorescent LEL may also suitably include an electron-transporting material (it will be discussed thereafter), as long as it has a triplet energy higher than that of the phosphorescent dopant.

In addition to the aforementioned hole-transporting materials in the HTL 132, there are several other classes of hole-transporting materials suitable for use as the host in a phosphorescent LEL.

One desirable host comprises a hole-transporting material of formula (F):

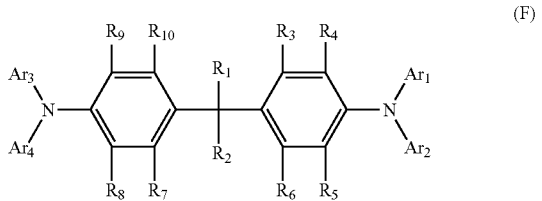

(F)

In formula (F), $R_1$ and $R_2$ represent substituents, provided that $R_1$ and $R_2$ can join to form a ring. For example, $R_1$ and $R_2$ can be methyl groups or join to form a cyclohexyl ring;

$Ar_1$-$Ar_4$ represent independently selected aromatic groups, for example phenyl groups or tolyl groups;

$R_3$-$R_{10}$ independently represent hydrogen, alkyl, substituted alkyl, aryl, substituted aryl group.

Examples of suitable materials include, but are not limited to:

1,1-Bis(4-(N,N-di-p-tolylamino)phenyl)cyclohexane (TAPC);
1,1-Bis(4-(N,N-di-p-tolylamino)phenyl)cyclopentane;
4,4'-(9H-fluoren-9-ylidene)bis[N,N-bis(4-methylphenyl)-benzenamine;
1,1-Bis(4-(N,N-di-p-tolylamino)phenyl)-4-phenylcyclohexane;
1,1-Bis(4-(N,N-di-p-tolylamino)phenyl)-4-methylcyclohexane;
1,1-Bis(4-(N,N-di-p-tolylamino)phenyl)-3-phenylpropane;
Bis[4-(N,N-diethylamino)-2-methylphenyl](4-methylphenyl)ethane;
Bis[4-(N,N-diethylamino)-2-methylphenyl](4-methylphenyl)ethane;
4-(4-Diethylaminophenyl)triphenylmethane;
4,4'-Bis(4-diethylaminophenyl)diphenylmethane.

A useful class of triarylamines suitable for use as the host includes carbazole derivatives such as those represented by formula (G):

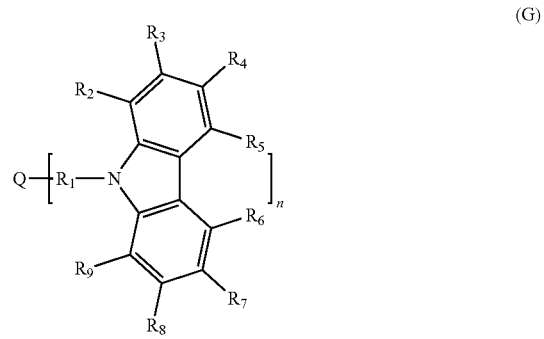

(G)

In formula (G), Q independently represents nitrogen, carbon, an aryl group, or substituted aryl group, preferably a phenyl group;

$R_1$ is preferably an aryl or substituted aryl group, and more preferably a phenyl group, substituted phenyl, biphenyl, substituted biphenyl group;

$R_2$ through $R_7$ are independently hydrogen, alkyl, phenyl or substituted phenyl group, aryl amine, carbazole, or substituted carbazole;

and n is selected from 1 to 4.

Another useful class of carbazoles satisfying structural formula (G) is represented by formula (C):

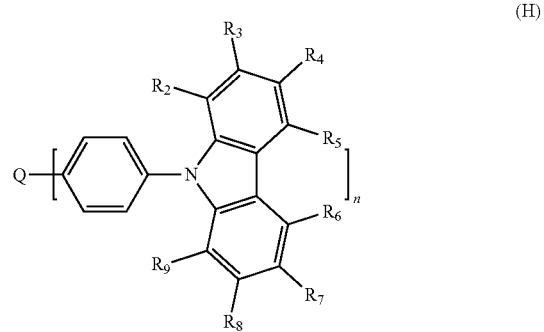

(H)

wherein:

n is an integer from 1 to 4;

Q is nitrogen, carbon, an aryl, or substituted aryl;

$R_2$ through $R_7$ are independently hydrogen, an alkyl group, phenyl or substituted phenyl, an aryl amine, a carbazole and substituted carbazole.

Illustrative of useful substituted carbazoles are the following:

4-(9H-carbazol-9-yl)-N,N-bis[4-(9H-carbazol-9-yl)phenyl]-benzenamine (TCTA);
4-(3-phenyl-9H-carbazol-9-yl)-N,N-bis[4(3-phenyl-9H-carbazol-9-yl)phenyl]-benzenamine;
9,9'-[5'-[4-(9H-carbazol-9-yl)phenyl][1,1':3',1''-terphenyl]-4,4''-diyl]bis-9H-carbazole.

9,9'-(2,2'-dimethyl[1,1'-biphenyl]-4,4'-diyl)bis-9H-carbazole (CDBP);

9,9'-[1,1'-biphenyl]-4,4'-diylbis-9H-carbazole (CBP);

9,9'-(1,3-phenylene)bis-9H-carbazole (mCP);

9,9'-(1,4-phenylene)bis-9H-carbazole;

9,9',9''-(1,3,5-benzenetriyl)tris-9H-carbazole;

9,9'-(1,4-phenylene)bis[N,N,N',N'-tetraphenyl-9H-carbazole-3,6-diamine;

9-[4-(9H-carbazol-9-yl)phenyl]-N,N-diphenyl-9H-carbazol-3-amine;

9,9'-(1,4-phenylene)bis[N,N-diphenyl-9H-carbazol-3-amine;

9-[4-(9H-carbazol-9-yl)phenyl]-N,N,N',N'-tetraphenyl-9H-carbazole-3,6-diamine.

The above classes of hosts suitable for phosphorescent LELs may also be used as hosts in fluorescent LELs as well.

Suitable phosphorescent dopants for use in a phosphorescent LEL can be selected from the phosphorescent materials described by formula (J) below:

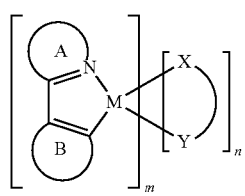

(J)

wherein:

A is a substituted or unsubstituted heterocyclic ring containing at least one nitrogen atom;

B is a substituted or unsubstituted aromatic or heteroaromatic ring, or ring containing a vinyl carbon bonded to M;

X-Y is an anionic bidentate ligand;

m is an integer from 1 to 3 and n in an integer from 0 to 2 such that m+n=3 for M=Rh or Ir; or m is an integer from 1 to 2 and n in an integer from 0 to 1 such that m+n=2 for M=Pt or Pd.

Compounds according to formula (J) may be referred to as C,N— (or C^N—) cyclometallated complexes to indicate that the central metal atom is contained in a cyclic unit formed by bonding the metal atom to carbon and nitrogen atoms of one or more ligands. Examples of heterocyclic ring A in formula (J) include substituted or unsubstituted pyridine, quinoline, isoquinoline, pyrimidine, indole, indazole, thiazole, and oxazole rings. Examples of ring B in formula (J) include substituted or unsubstituted phenyl, napthyl, thienyl, benzothienyl, furanyl rings. Ring B in formula (J) may also be a N-containing ring such as pyridine, with the proviso that the N-containing ring bonds to M through a C atom as shown in formula (J) and not the N atom.

An example of a tris-C,N-cyclometallated complex according to formula (J) with m=3 and n=0 is tris(2-phenyl-pyridinato-N,C$^{2'}$)Iridium (III), shown below in stereodiagrams as facial (fac-) or meridional (mer-)isomers.

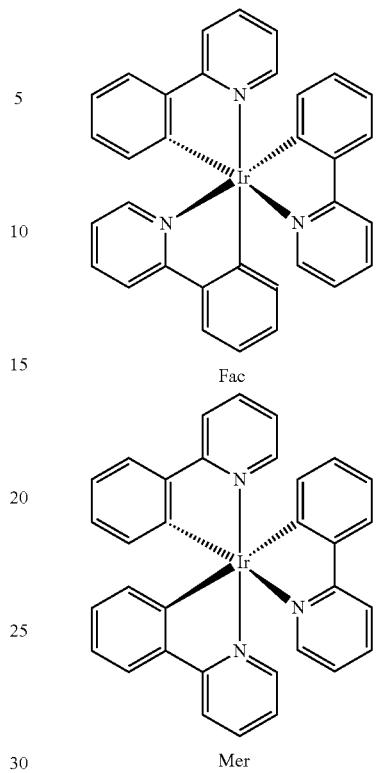

Generally, facial isomers are preferred since they are often found to have higher phosphorescent quantum yields than the meridional isomers. Additional examples of tris-C,N-cyclometallated phosphorescent materials according to formula (J) are tris(2-(4'-methylphenyl)pyridinato-N,C$^{2'}$)Iridium(III), tris(3-phenylisoquinolinato-N,C$^{2'}$)Iridium(III), tris(2-phenylquinolinato-N,C$^{2'}$)Iridium(III), tris(1-phenylisoquinolinato-N,C$^{2'}$)Iridium(III), tris(1-(4'-methylphenyl)isoquinolinato-N,C$^{2'}$)Iridium(III), tris(2-(4',6'-diflourophenyl)-pyridinato-N,C$^{2'}$)Iridium(III), tris(2-((5'-phenyl)-phenyl)pyridinato-N,C$^{2'}$)Iridium(III), tris(2-(2'-benzothienyl)pyridinato-N,C$^{3'}$)Iridium(III), tris(2-phenyl-3,3'dimethyl)indolato-N,C$^{2'}$)Ir(III), tris(1-phenyl-1H-indazolato-N,C$^{2'}$)Ir(III).

Of these, tris(1-phenylisoquinoline)iridium (III) (also referred to as Ir(piq)$_3$) and tris(2-phenylpyridine)iridium (also referred to as Ir(ppy)$_3$) are particularly suitable for this invention.

Tris-C,N-cyclometallated phosphorescent materials also include compounds according to formula (J) wherein the monoanionic bidentate ligand X-Y is another C,N-cyclometallating ligand. Examples include bis(1-phenylisoquinolinato-N,C$^{2'}$)(2-phenylpyridinato-N,C$^{2'}$)Iridium(III) and bis(2-phenylpyridinato-N,C$^{2'}$)(1-phenylisoquinolinato-N,C'$^2$) Iridium(III). Synthesis of such tris-C,N-cyclometallated complexes containing two different C,N-cyclometallating ligands may be conveniently synthesized by the following steps. First, a bis-C,N-cyclometallated diiridium dihalide complex (or analogous dirhodium complex) is made according to the method of Nonoyama (Bull. Chem. Soc. Jpn., 47, 767 (1974)). Secondly, a zinc complex of the second, dissimilar C,N-cyclometallating ligand is prepared by reaction of a zinc halide with a lithium complex or Grignard reagent of the cyclometallating ligand. Third, the thus formed zinc complex of the second C,N-cyclometallating ligand is reacted with the previously obtained bis-C,N-cyclometallated diiridium dihalide complex to form a tris-C,N-cyclometallated complex containing the two different C,N-cyclometallating ligands. Desirably, the thus obtained tris-C,N-cyclometallated complex containing the two different C,N-cyclometallating ligands may be converted to an isomer wherein the C atoms bonded to the metal (e.g. Ir) are all mutually cis by heating in a suitable solvent such as dimethyl sulfoxide.

Suitable phosphorescent materials according to formula (J) may in addition to the C,N-cyclometallating ligand(s) also contain monoanionic bidentate ligand(s) X-Y that are not C,N-cyclometallating. Common examples are beta-diketonates such as acetylacetonate, and Schiff bases such as picolinate. Examples of such mixed ligand complexes according to formula (J) include bis(2-phenylpyridinato-N,$C^{2'}$)Iridium (III)(acetylacetonate), bis(2-(2'-benzothienyl)pyridinato-N, $C^{3'}$)Iridium(III)(acetylacetonate), and bis(2-(4',6'-difluorophenyl)-pyridinato-N,$C^{2'}$)Iridium(III)(picolinate).

Other important phosphorescent materials according to formula (J) include C,N-cyclometallated Pt(II) complexes such as cis-bis(2-phenylpyridinato-N,$C^{2'}$)platinum(II), cis-bis(2-(2'-thienyl)pyridinato-N,$C^{3'}$)platinum(II), cis-bis(2-(2'-thienyl)quinolinato-N,$C^{5'}$)platinum(II), or (2-(4',6'-difluorophenyl)pyridinato-N,$C^{2'}$)platinum (II) (acetylacetonate).

The emission wavelengths (color) of C,N-cyclometallated phosphorescent materials according to formula (J) are governed principally by the lowest energy optical transition of the complex and hence by the choice of the C,N-cyclometallating ligand. For example, 2-phenyl-pyridinato-N,$C^{2'}$ complexes are typically green emissive while 1-phenyl-isoquinolinolato-N,$C^{2'}$ complexes are typically red emissive. In the case of complexes having more than one C,N-cyclometallating ligand, the emission will be that of the ligand having the property of longest wavelength emission. Emission wavelengths may be further shifted by the effects of substituent groups on the C,N-cyclometallating ligands. For example, substitution of electron donating groups at appropriate positions on the N-containing ring A or electron accepting groups on the C-containing ring B tend to blue-shift the emission relative to the unsubstituted C,N-cyclometallated ligand complex. Selecting a monodentate anionic ligand X,Y in formula (J) having more electron accepting properties also tends to blue-shift the emission of a C,N-cyclometallated ligand complex. Examples of complexes having both monoanionic bidentate ligands possessing electron accepting properties and electron accepting substituent groups on the C-containing ring B include bis(2-(4',6'-difluorophenyl)-pyridinato-N,$C^{2'}$)iridium(III)(picolinate) and bis(2-(4',6'-difluorophenyl)-pyridinato-N,$C^{2'}$)iridium(III)(tetrakis(1-pyrazolyl)borate).

The central metal atom in phosphorescent materials according to formula (J) may be Rh or Ir (m+n=3) and Pd or Pt (m+n=2). Preferred metal atoms are Ir and Pt since they tend to give higher phosphorescent quantum efficiencies according to the stronger spin-orbit coupling interactions generally obtained with elements in the third transition series.

In addition to bidentate C,N-cyclometallating complexes represented by formula (J), many suitable phosphorescent materials contain multidentate C,N-cyclometallating ligands. Phosphorescent materials having tridentate ligands suitable for use in the present invention are disclosed in U.S. Pat. No. 6,824,895 B1 and references therein, incorporated in their entirety herein by reference. Phosphorescent materials having tetradentate ligands suitable for use in the present invention are described by the following formulae:

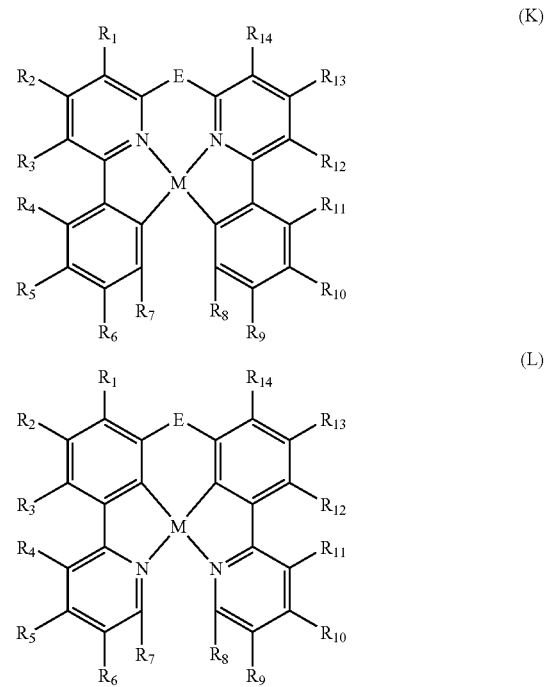

wherein:

M is Pt or Pd;

$R^1$-$R^7$ represent hydrogen or independently selected substituents, provided that $R^1$ and $R^2$, $R^2$ and $R^3$, $R^3$ and $R^4$, $R^4$ and $R^5$, $R^5$ and $R^6$, as well as $R^6$ may join to form a ring group;

$R^8$-$R^{14}$ represent hydrogen or independently selected substituents, provided that $R^8$ and $R^9$, $R^9$ and $R^{10}$, $R^{10}$ and $R^{11}$, $R^{11}$ and $R^{12}$, $R^{12}$ and $R^{13}$, as well as $R^{13}$ and $R^{14}$, may join to form a ring group;

E represents a bridging group selected from the following:

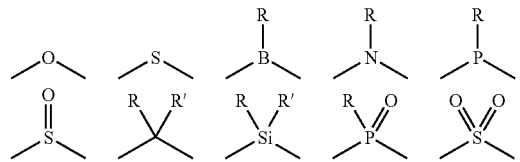

wherein:

R and R' represent hydrogen or independently selected substituents; provided R and R' may combine to form a ring group.

One desirable tetradentate C,N-cyclometallated phosphorescent material suitable for use in as the phosphorescent dopant is represented by the following formula:

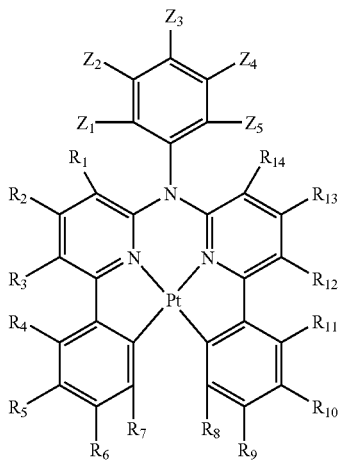

(M)

wherein:

R$^1$—R$^7$ represent hydrogen or independently selected substituents, provided is that R$^1$ and R$^2$, R$^2$ and R$^3$, R$^3$ and R$^4$, R$^4$ and R$^5$, R$^5$ and R$^6$, as well as R$^6$ and R$^7$ may combine to form a ring group;

R$^8$—R$^{14}$ represent hydrogen or independently selected substituents, provided that R$^8$ and R$^9$, R$^9$ and R$^{10}$, R$^{10}$ and R$^{11}$, R$^{11}$ and R$^{12}$, R$^{12}$ and R$^{13}$, as well as R$^{13}$ and R$^{14}$ may combine to form a ring group;

Z$^1$—Z$^5$ represent hydrogen or independently selected substituents, provided that Z$^1$ and Z$^2$, Z$^2$ and Z$^3$, Z$^3$ and Z$^4$, as well as Z$^4$ and Z$^5$ may combine to form a ring group.

Specific examples of phosphorescent materials having tetradentate C,N-cyclometallating ligands suitable for use in the present invention include compounds (M-1), (M-2) and (M-3) represented below.

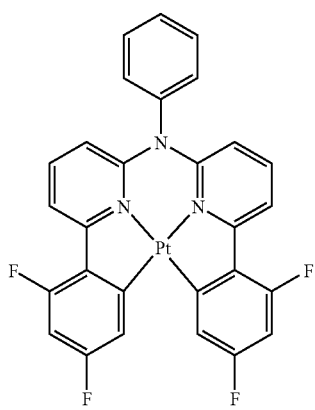

(M-1)

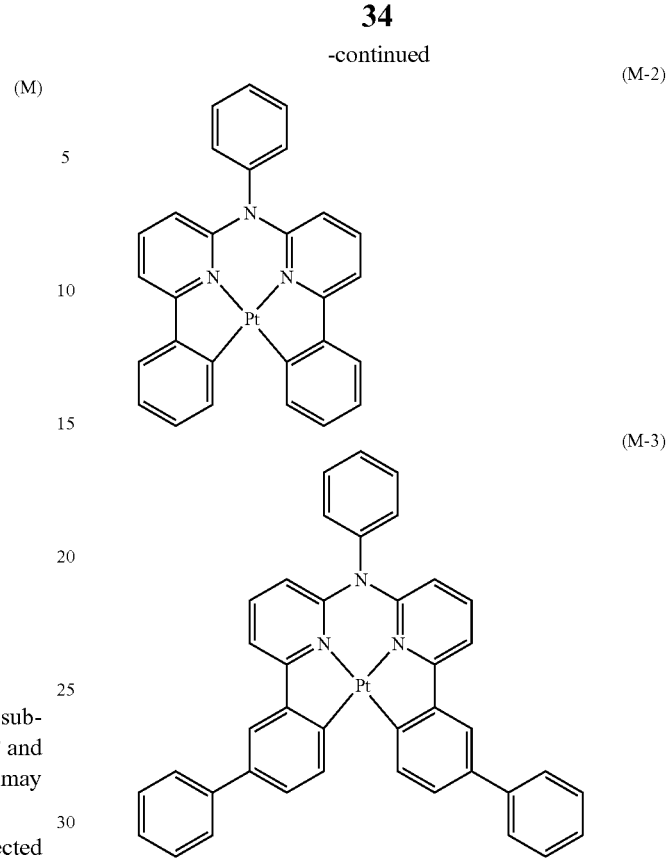

Phosphorescent materials having tetradentate C,N-cyclometallating ligands may be synthesized by reacting the tetradentate C,N-cyclometallating ligand with a salt of the desired metal, such as K$_2$PtCl$_4$, in a proper organic solvent such as glacial acetic acid to form the phosphorescent material having tetradentate C,N-cyclometallating ligands. A tetraalkylammonium salt such as tetrabutylammonium chloride can be used as a phase transfer catalyst to accelerate the reaction.

Other phosphorescent materials that do not involve C,N-cyclometallating ligands are known. Phosphorescent complexes of Pt(II), Ir(I), and Rh(I) with maleonitriledithiolate have been reported (Johnson et al., *J. Am. Chem. Soc.*, 105, 1795 (1983)). Re(I) tricarbonyl diimine complexes are also known to be highly phosphorescent (Wrighton and Morse, *J. Am. Chem. Soc.*, 96, 998 (1974); Stufkens, *Comments Inorg. Chem.*, 13, 359 (1992); Yam, *Chem. Commun.*, 789 (2001)). Os(II) complexes containing a combination of ligands including cyano ligands and bipyridyl or phenanthroline ligands have also been demonstrated in a polymer OLED (Ma et al., *Synthetic Metals*, 94, 245 (1998)).

Porphyrin complexes such as 2,3,7,8,12,13,17,18-octaethyl-21H, 23H-porphine platinum(II) are also useful phosphorescent dopant.

Still other examples of useful phosphorescent materials include coordination complexes of the trivalent lanthanides such as Tb$^{3+}$ and Eu$^{3+}$ (Kido et al., *Chem. Lett.*, 657 (1990); *J. Alloys and Compounds*, 192, 30 (1993); *Jpn. J. Appl. Phys.*, 35, L394 (1996) and *Appl. Phys. Lett.*, 65, 2124 (1994)).

The phosphorescent dopant in a phosphorescent LEL is typically present in an amount of from 1 to 20% by volume of the LEL, and conveniently from 2 to 8% by volume of the LEL. In some embodiments, the phosphorescent dopant(s) may be attached to one or more host materials. The host materials may further be polymers. The phosphorescent dopant in the first phosphorescent light-emitting layer is selected from green and red phosphorescent materials.

The thickness of a phosphorescent LEL is greater than 0.5 nm, preferably, in the range of from 1.0 nm to 40 nm.

b) Fluorescent light emitting layers

Although the term "fluorescent" is commonly used to describe any light-emitting material, in this case it refers to a material that emits light from a singlet excited state. Fluorescent materials may be used in the same layer as the phosphorescent material, in adjacent layers, in adjacent pixels, or any combination. Care must be taken not to select materials that will adversely affect the performance of the phosphorescent materials of this invention. One skilled in the art will understand that concentrations and triplet energies of materials in the same layer as the phosphorescent material or in an adjacent layer must be appropriately set so as to prevent unwanted quenching of the phosphorescence.

Typically, a fluorescent LEL includes at least one host and at least one fluorescent dopant. The host may be a hole-transporting material or any of the suitable hosts for phosphorescent dopants as defined above or may be an electron-transporting material as defined below.

The dopant is typically chosen from highly fluorescent dyes, e.g., transition metal complexes as described in WO 98/55561 A1, WO 00/18851 A1, WO 00/57676 A1, and WO 00/70655.

Useful fluorescent dopants include, but are not limited to, derivatives of anthracene, tetracene, xanthene, perylene, phenylene, dicyanomethylenepyran compounds, thiopyran compounds, polymethine compounds, pyrylium and thiapyrylium compounds, arylpyrene compounds, arylenevinylene compounds, periflanthene derivatives, indenoperylene derivatives, bis(azinyl)amine boron compounds, bis(azinyl)methane boron compounds, distryrylbenzene derivatives, distyrylbiphenyl derivatives, distyrylamine derivatives and carbostryl compounds.

Some fluorescent emitting materials include, but are not limited to, derivatives of anthracene, tetracene, xanthene, perylene, rubrene, coumarin, rhodamine, and quinacridone, dicyanomethylenepyran compounds, thiopyran compounds, polymethine compounds, pyrylium and thiapyrylium compounds, fluorene derivatives, periflanthene derivatives, indenoperylene derivatives, bis(azinyl)amine boron compounds, bis(azinyl)methane compounds (as described in U.S. Pat. No. 5,121,029) and carbostyryl compounds. Illustrative examples of useful materials include, but are not limited to, the following:

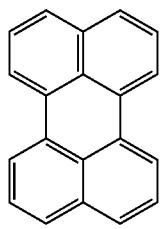

FD-1

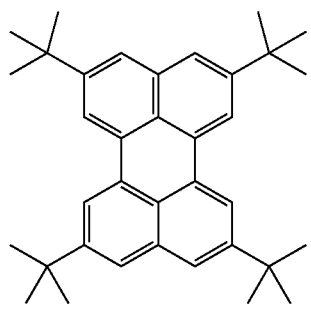

FD-2

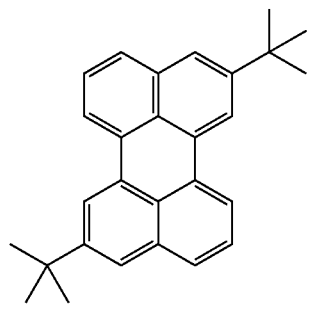

FD-3

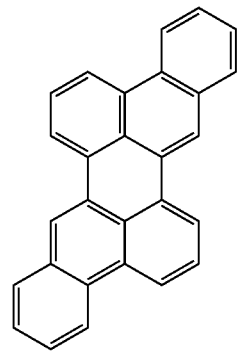

FD-4

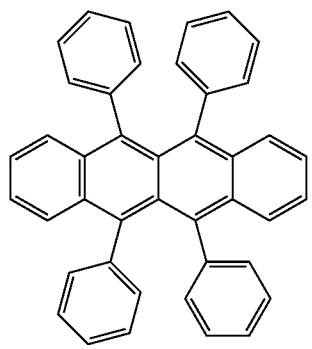

FD-5

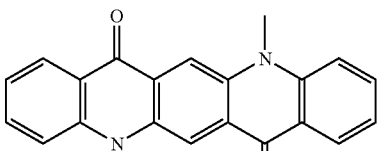

FD-6

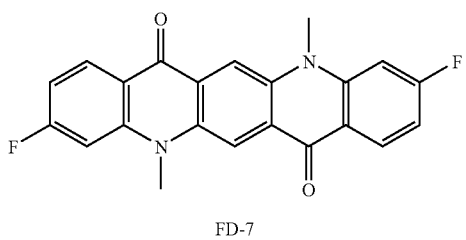 [SMILES: Cn1c2cc(F)ccc2c(=O)c2cc3c(cc21)c(=O)c1ccc(F)cc1n3C ; "FD-7"]

FD-7

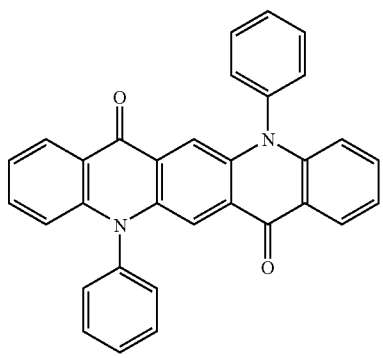

FD-8

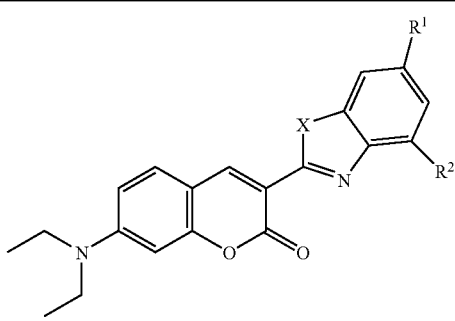

|       | X | R1     | R2     |
|-------|---|--------|--------|
| FD-9  | O | H      | H      |
| FD-10 | O | H      | Methyl |
| FD-11 | O | Methyl | H      |
| FD-12 | O | Methyl | Methyl |
| FD-13 | O | H      | t-butyl|
| FD-14 | O | t-butyl| H      |
| FD-15 | O | t-butyl| t-butyl|
| FD-16 | S | H      | H      |
| FD-17 | S | H      | Methyl |
| FD-18 | S | Methyl | H      |
| FD-19 | S | Methyl | Methyl |
| FD-20 | S | H      | t-butyl|
| FD-21 | S | t-butyl| H      |
| FD-22 | S | t-butyl| t-butyl|

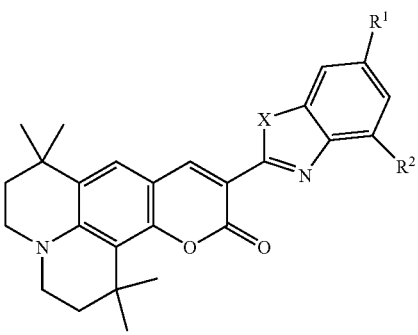

|       | X | R1     | R2     |
|-------|---|--------|--------|
| FD-13 | O | H      | H      |
| FD-24 | O | H      | Methyl |
| FD-25 | O | Methyl | H      |
| FD-26 | O | Methyl | Methyl |
| FD-27 | O | H      | t-butyl|
| FD-28 | O | t-butyl| H      |
| FD-29 | O | t-butyl| t-butyl|
| FD-30 | S | H      | H      |
| FD-31 | S | H      | Methyl |
| FD-32 | S | Methyl | H      |
| FD-33 | S | Methyl | Methyl |
| FD-34 | S | H      | t-butyl|
| FD-35 | S | t-butyl| H      |
| FD-36 | S | t-butyl| t-butyl|

|       | R       |
|-------|---------|
| FD-37 | phenyl  |
| FD-38 | methyl  |
| FD-39 | t-butyl |
| FD-40 | mesityl |

|       | R      |
|-------|--------|
| FD-41 | phenyl |
| FD-42 | methyl |

| | |
|---|---|
| FD-43 | t-butyl |
| FD-44 | mesityl |
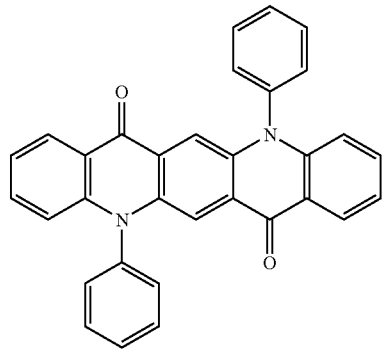
FD-45
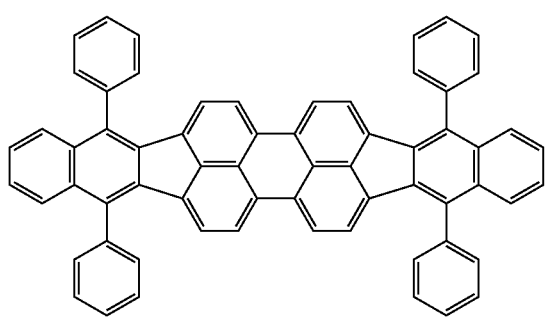
FD-46
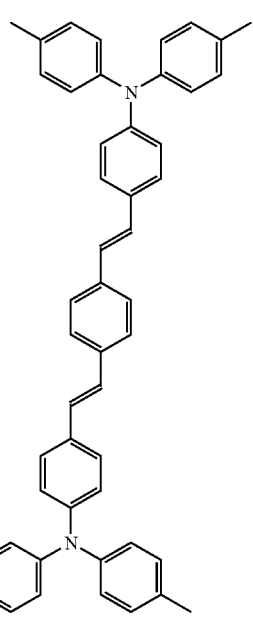
FD-47
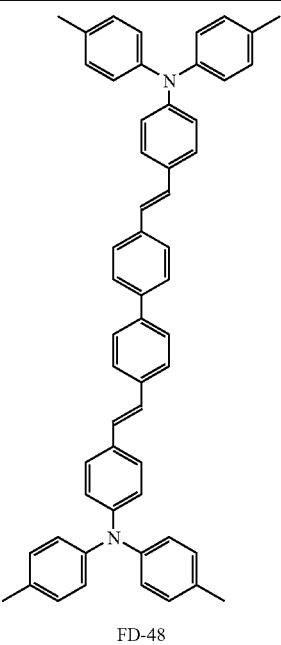
FD-48
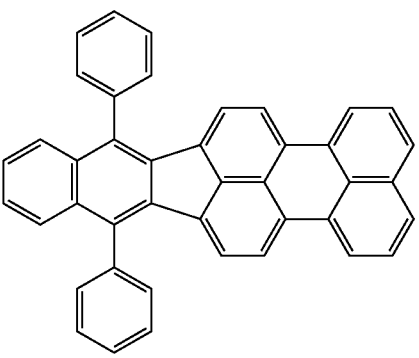
FD-49
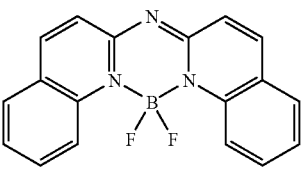
FD-50
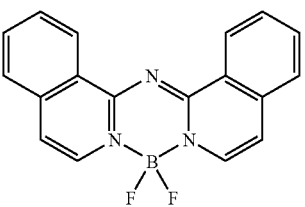
FD-51

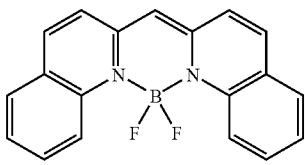

FD-52

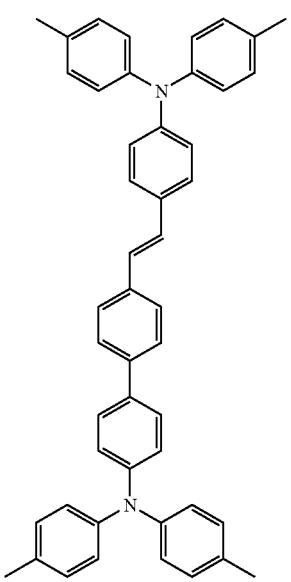

FD-53

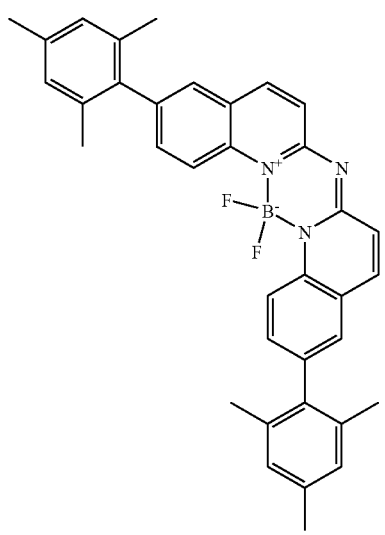

FD-54

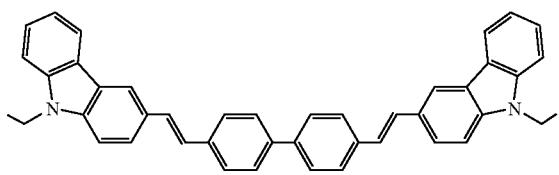

FD-55

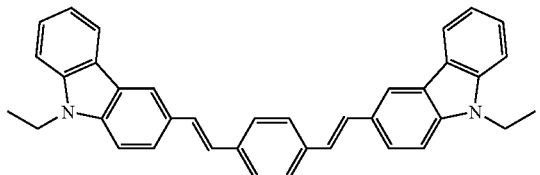

FD-56

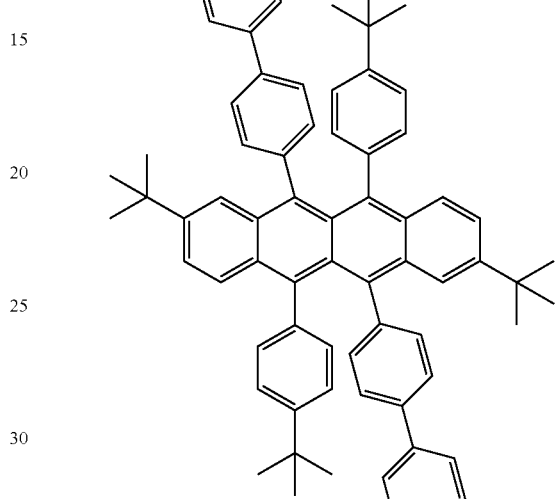

FD-57

Preferred fluorescent blue dopants may be found in Chen, Shi, and Tang, "Recent Developments in Molecular Organic Electroluminescent Materials," Macromol. Symp. 125, 1 (1997) and the references cited therein; Hung and Chen, "Recent Progress of Molecular Organic Electroluminescent Materials and Devices," Mat. Sci. and Eng. R39, 143 (2002) and the references cited therein. It should be noted that FD-46 and FD-49 are fluoranthene derivatives with annulated rings.

A particularly preferred class of blue-emitting fluorescent dopants is represented by Formula (N), known as a bis(azinyl) amine borane complex, and is described in U.S. Pat. No. 6,661,023.

Formula (N)

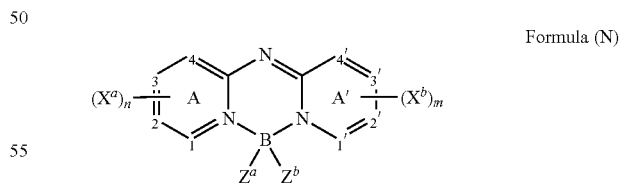

wherein:
  A and A' represent independent azine ring systems corresponding to 6-membered aromatic ring systems containing at least one nitrogen;
  each $X^a$ and $X^b$ is an independently selected substituent, two of which may join to form a fused ring to A or A';
  m and n are independently 0 to 4;
  $Z^a$ and $Z^b$ are independently selected substituents; and
  1, 2, 3, 4, 1', 2', 3', and 4' are independently selected as either carbon or nitrogen atoms.

Desirably, the azine rings are either quinolinyl or isoquinolinyl rings such that 1, 2, 3, 4, 1', 2', 3', and 4' are all carbon; m and n are equal to or greater than 2; and $X^a$ and $X^b$ represent at least two carbon substituents which join to form an aromatic ring. Desirably, $Z^a$ and $Z^b$ are fluorine atoms.

Preferred embodiments further include devices where the two fused ring systems are quinoline or isoquinoline systems; the aryl or heterocyclic substituent is a phenyl group; there are present at least two $X^a$ groups and two $X^b$ groups which join to form a 6-6 fused ring, the fused ring systems are fused at the 1-2, 3-4, 1'-2', or 3'-4' positions, respectively, one or both of the fused rings is substituted by a phenyl group; and where the dopant is depicted in Formulae (N-a), (N-b), or (N-c).

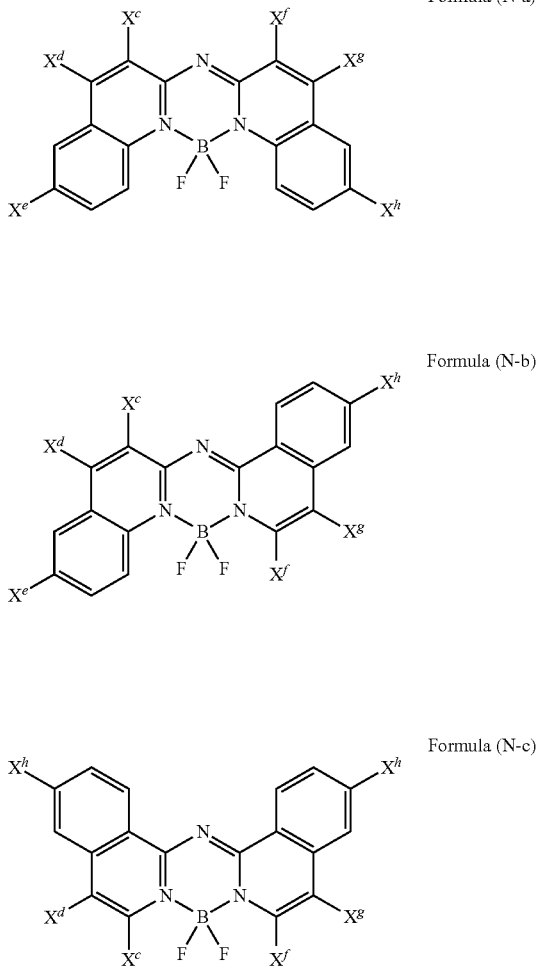

Formula (N-a)

Formula (N-b)

Formula (N-c)

wherein:
each $X^c$, $X^d$, $X^e$, $X^f$, $X^g$, and $X^h$ is hydrogen or an independently selected substituent, one of which must be an aryl or heterocyclic group.

Desirably, the azine rings are either quinolinyl or isoquinolinyl rings such that 1, 2, 3, 4, 1', 2', 3', and 4' are all carbon; m and n are equal to or greater than 2; and $X^a$ and $X^b$ represent at least two carbon substituents which join to form an aromatic ring, and one is an aryl or substituted aryl group. Desirably, $Z^a$ and $Z^b$ are fluorine atoms.

Of these, compound FD-54 is particularly useful.

Coumarins represent a useful class of green-emitting dopants as described by Tang et al. in U.S. Pat. Nos. 4,769,292 and 6,020,078. Green dopants or light-emitting materials can be coated as 0.01 to 50% by weight into the host material, but typically coated as 0.01 to 30% and more typically coated as 0.01 to 15% by weight into the host material. Examples of useful green-emitting coumarins include C545T and C545TB. Quinacridones represent another useful class of green-emitting dopants. Useful quinacridones are described in U.S. Pat. No. 5,593,788, publication JP 09-13026A, and commonly assigned U.S. patent application Ser. No. 10/184,356 filed Jun. 27, 2002 by Lelia Cosimbescu, entitled "Device Containing Green Organic Light-Emitting Diode" the disclosure of which is incorporated herein.

Examples of particularly useful green-emitting quinacridones are FD-7 and FD-8.

Formula (N-d) below represents another class of green-emitting dopants useful in the invention.

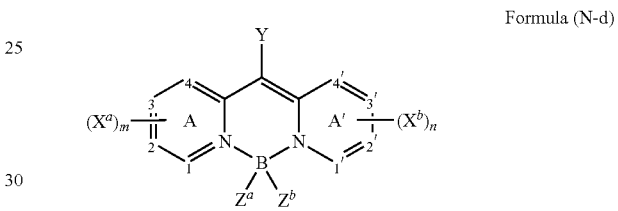

Formula (N-d)

wherein:
A and A' represent independent azine ring systems corresponding to 6-membered aromatic ring systems containing at least one nitrogen;
each $X^a$ and $X^b$ is an independently selected substituent, two of which may join to form a fused ring to A or A';
m and n are independently 0 to 4;
Y is H or a substituent;
$Z^a$ and $Z^b$ are independently selected substituents; and
1, 2, 3, 4, 1', 2', 3', and 4' are independently selected as either carbon or nitrogen atoms.

In the device, 1, 2, 3, 4, 1', 2', 3', and 4' are conveniently all carbon atoms. The device may desirably contain at least one or both of ring A or A' that contains substituents joined to form a fused ring. In one useful embodiment there is present at least one $X^a$ or $X^b$ group selected from the group consisting of halide and alkyl, aryl, alkoxy, and aryloxy groups. In another embodiment, there is present a $Z^a$ and $Z^b$ group independently selected from the group consisting of fluorine and alkyl, aryl, alkoxy and aryloxy groups. A desirable embodiment is where $Z^a$ and $Z^b$ are F. Y is suitably hydrogen or a substituent such as an alkyl, aryl, or heterocyclic group.

The emission wavelength of these compounds may be adjusted to some extent by appropriate substitution around the central bis(azinyl)methene boron group to meet a color aim, namely green. Some examples of useful material are FD-50, FD-51 and FD-52.

Naphthacenes and derivatives thereof also represent a useful class of emitting dopants, which can also be used as stabilizers. These dopant materials can be coated as 0.01 to 50% by weight into the host material, but typically coated as 0.01 to 30% and more typically coated as 0.01 to 15% by weight into the host material. Naphthacene derivative YD-1 (t-BuDPN) below, is an example of a dopant material used as a stabilizer.

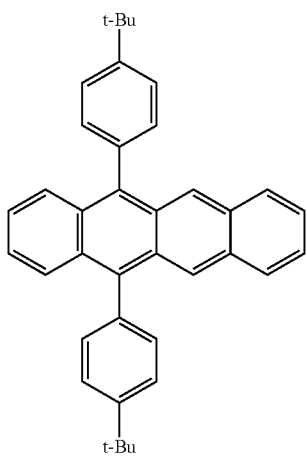

YD-1

Some examples of this class of materials are also suitable as host materials as well as dopants. For example, see U.S. Pat. No. 6,773,832 or U.S. Pat. No. 6,720,092. A specific example of this would be rubrene (FD-5).

Another class of useful dopants are perylene derivatives; for example see U.S. Pat. No. 6,689,493. A specific examples is FD-46.

Metal complexes of 8-hydroxyquinoline and similar derivatives (Formula O) constitute one class of useful non-electroluminescent host compounds capable of supporting electroluminescence, and are particularly suitable for light emission of wavelengths longer than 500 nm, e.g., green, yellow, orange, and red.

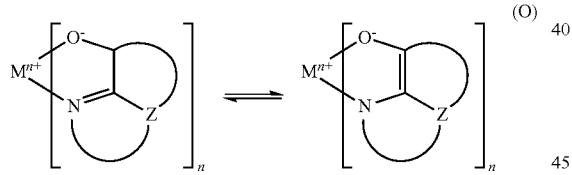

(O)

wherein:
M represents a metal;
n is an integer of from 1 to 4; and
Z independently in each occurrence represents the atoms completing a nucleus having at least two fused aromatic rings.

From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such as aluminum or gallium, or a transition metal such as zinc or zirconium. Generally any monovalent, divalent, trivalent, or tetravalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:

O-1: Aluminum trisoxine[alias, tris(8-quinolinolato)aluminum(III)]

O-2: Magnesium bisoxine[alias, bis(8-quinolinolato)magnesium(II)]

O-3: Bis[benzo{f}-8-quinolinolato]zinc (II)

O-4: Bis(2-methyl-8-quinolinolato)aluminum(III)-μ-oxo-bis(2-methyl-8-quinolinolato)aluminum(III)

O-5: Indium trisoxine[alias, tris(8-quinolinolato)indium]

O-6: Aluminum tris(5-methyloxine)[alias, tris(5-methyl-8-quinolinolato)aluminum(III)]

O-7: Lithium oxine[alias, (8-quinolinolato)lithium(I)]

O-8: Gallium oxine[alias, tris(8-quinolinolato)gallium (III)]

O-9: Zirconium oxine[alias, tetra(8-quinolinolato)zirconium(IV)]

O-10: Bis(2-methyl-8-quinolinato)-4-phenylphenolatoaluminum(III)

Anthracene derivatives according to formula (P) are also very useful host materials in the LEL:

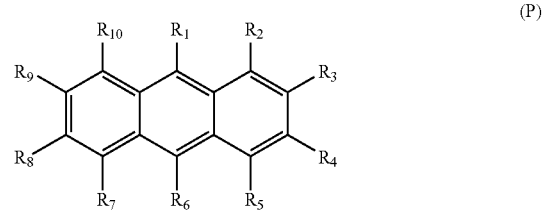

(P)

wherein:

$R_1$-$R_{10}$ are independently chosen from hydrogen, alkyl groups from 1-24 carbon atoms or aromatic groups from 1-24 carbon atoms. Particularly preferred are compounds where $R_1$ and $R_6$ are phenyl, biphenyl or napthyl, $R_3$ is phenyl, substituted phenyl or napthyl and $R_2$, $R_4$, $R_5$, $R_7$-$R_{10}$ are all hydrogen. Such anthracene hosts are known to have excellent electron transporting properties.

Particularly desirable are derivatives of 9,10-di-(2-naphthyl)anthracene. Illustrative examples include 9,10-di-(2-naphthyl)anthracene (ADN) and 2-t-butyl-9,10-di-(2-naphthyl)anthracene (TBADN). Other anthracene derivatives can be useful as a non-electroluminescent compound in the LEL, such as diphenylanthracene and its derivatives, as described in U.S. Pat. No. 5,927,247. Styrylarylene derivatives as described in U.S. Pat. No. 5,121,029 and JP 08333569 are also useful non-electroluminescent materials. For example, 9,10-bis[4-(2,2-diphenylethenyl)phenyl]anthracene, 4,4'-Bis (2,2-diphenylethenyl)-1,1'-biphenyl (DPVBi) and phenylanthracene derivatives as described in EP 681,019 are useful non-electroluminescent materials.

Some illustrative examples of suitable anthracenes are:

(P-1)
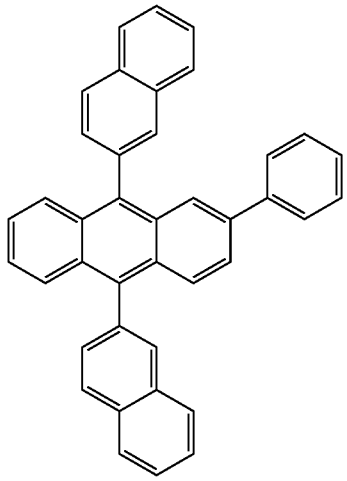

(P-2)
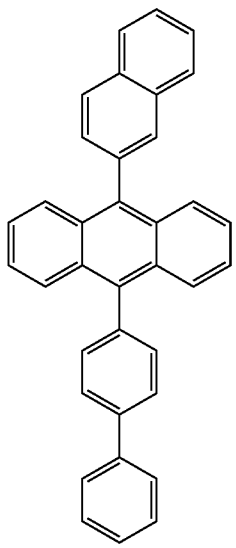

(P-3)
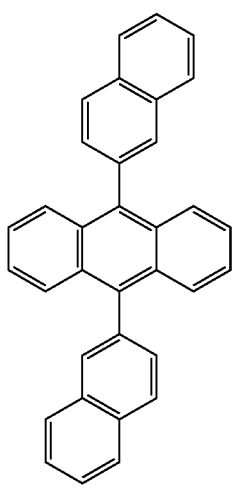

-continued (P-4)
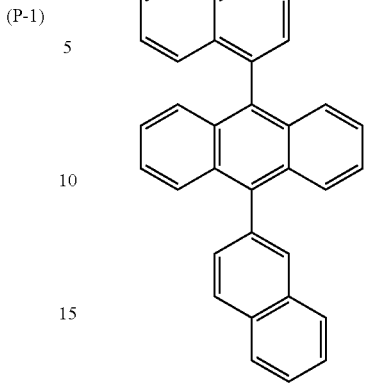

Spacer Layer

Spacer layers, when present, are located in direct contact to a LEL. They may be located on either the anode or cathode side, or even both sides of the LEL. They typically do not contain any light-emissive dopants. One or more materials may be used and could be either a hole-transporting material as defined above or an electron-transporting material as defined below. If located next to a phosphorescent LEL, the material in the spacer layer should have higher triplet energy than that of the phosphorescent dopant in the LEL. Most desirably, the material in the spacer layer will be the same as used as the host in the adjacent LEL. Thus, any of the host materials described as also suitable for use in a spacer layer. The spacer layer should be thin; at least 0.1 nm, but preferably in the range of from 1.0 nm to 20 nm.

Hole-Blocking Layer (HBL)

When a LEL containing a phosphorescent emitter is present, it is desirable to locate a hole-blocking layer 135 between the electron-transporting layer 136 and the light-emitting layer 134 to help confine the excitons and recombination events to the LEL. In this case, there should be an energy barrier for hole migration from co-hosts into the hole-blocking layer, while electrons should pass readily from the hole-blocking layer into the light-emitting layer comprising co-host materials and a phosphorescent emitter. It is further desirable that the triplet energy of the hole-blocking material be greater than that of the phosphorescent material. Suitable hole-blocking materials are described in WO 00/70655A2, WO 01/41512 and WO 01/93642 A1. Two examples of useful hole-blocking materials are bathocuproine (BCP) and bis(2-methyl-8-quinolinolato)(4-phenylphenolato)aluminum(III) (BAlq). Metal complexes other than BAlq are also known to block holes and excitons as described in US 20030068528. When a hole-blocking layer is used, its thickness can be between 2 and 100 nm and suitably between 5 and 10 nm.

Electron Transporting Layer

The purpose of an electron-transporting layer is to allow efficient movement of electrons from the cathode to the LEL. As such, it does not emit substantial amounts of light.

In one embodiment, the electron-transporting layer 136 may be composed only of the fluoranthene derivative or may be a mixture of the fluoranthene with other appropriate materials. The % volume ratio of fluoranthene to additional material can be anywhere from 1% to 99%, more suitably at least 10% and typically, at least 30%. The fluoranthene or any additional materials used may be the same or different than used as in the LEL. If an organic lithium EIM is present, it may be the same or different as used in the EIL.

The anthracene class of electron-transporting materials can also be used in the ETL with or without the fluoranthene of the invention. These anthracene electron transporting derivatives are represented by Formula (P) as described above in connection with host materials for a LEL. The anthracene in the ETL can be the same or different from that used in the LEL.

In addition to any of the electron-transporting materials previously described, any other materials known to be suitable for use in the ETL may be used. Included are, but are not limited to, chelated oxinoid compounds, anthracene derivatives, pyridine-based materials, imidazoles, oxazoles, thiazoles and their derivatives, polybenzobisazoles, cyano-containing polymers and perfluorinated materials. Other electron-transporting materials include various butadiene derivatives as disclosed in U.S. Pat. No. 4,356,429 and various heterocyclic optical brighteners as described in U.S. Pat. No. 4,539,507.

A preferred class of benzazoles is described by Shi et al. in U.S. Pat. Nos. 5,645,948 and 5,766,779. Such compounds are represented by structural formula (Q):

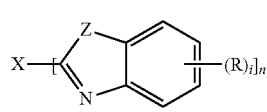

(Q)

In formula (Q), n is selected from 2 to 8 and i is selected from 1-5;

Z is independently O, NR or S;

R is individually hydrogen; alkyl of from 1 to 24 carbon atoms, for example, propyl, t-butyl, heptyl, and the like; aryl or hetero-atom substituted aryl of from 5 to 20 carbon atoms, for example, phenyl and naphthyl, furyl, thienyl, pyridyl, quinolinyl and other heterocyclic systems; or halo such as chloro, fluoro; or atoms necessary to complete a fused aromatic ring; and X is a linkage unit consisting of carbon, alkyl, aryl, substituted alkyl, or substituted aryl, which conjugately or unconjugately connects the multiple benzazoles together.

An example of a useful benzazole is 2,2',2''-(1,3,5-phenylene)tris[1-phenyl-1H-benzimidazole] (TPBI) represented by a formula (Q-1) shown below:

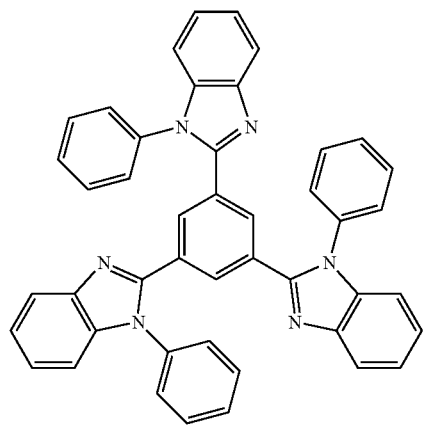

(Q-1)

Another suitable class of the electron-transporting materials includes various substituted phenanthrolines as represented by formula (R):

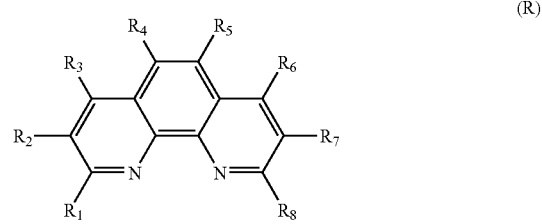

(R)

In formula (R), $R_1$-$R_8$ are independently hydrogen, alkyl group, aryl or substituted aryl group, and at least one of $R_1$-$R_8$ is aryl group or substituted aryl group.

Examples of suitable materials are 2,9-dimethyl-4,7-diphenylphenanthroline (BCP) (see formula (R-1)) and 4,7-diphenyl-1,10-phenanthroline (Bphen) (see formula (R-2)).

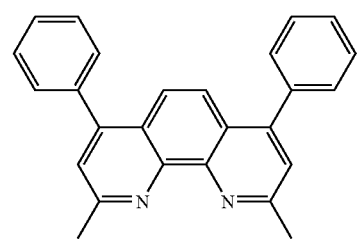

(R-1)

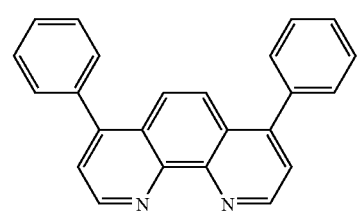

(R-2)

Suitable triarylboranes that function as an electron-transporting material may be selected from compounds having the chemical formula (S):

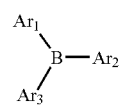

(S)

wherein:

$Ar_1$ to $Ar_3$ are independently an aromatic hydrocarbocyclic group or an aromatic heterocyclic group which may have a substituent. It is preferable that compounds having the above structure are selected from formula (S-1):

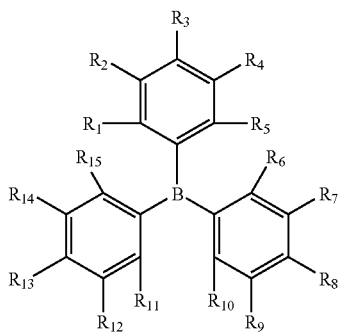

wherein:

$R_1$-$R_{15}$ are independently hydrogen, fluoro, cyano, trifluoromethyl, sulfonyl, alkyl, aryl or substituted aryl group.

Specific representative embodiments of the triarylboranes include:

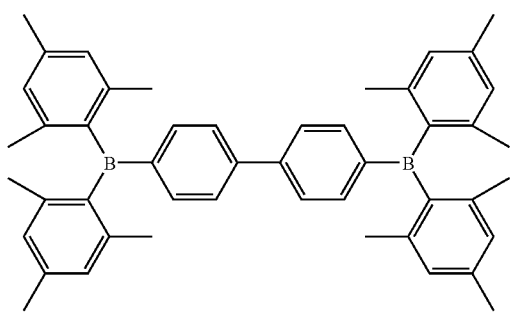

(S-1)

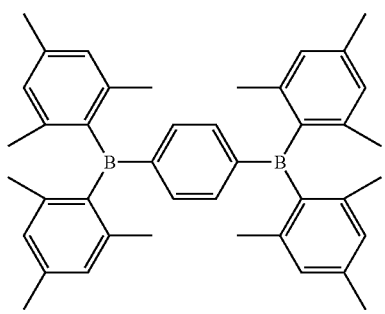

(S-2)

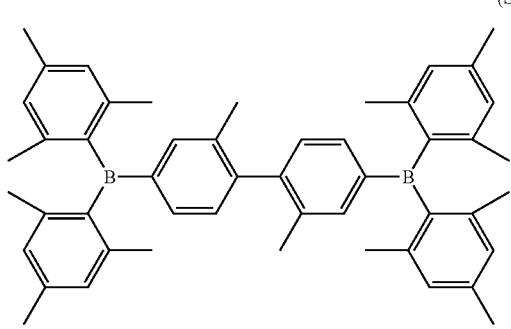

(S-3)

The electron-transporting material may also be selected from substituted 1,3,4-oxadiazoles of formula (T):

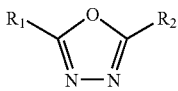

(T)

wherein:

$R_1$ and $R_2$ are individually hydrogen; alkyl of from 1 to 24 carbon atoms, for example, propyl, t-butyl, heptyl, and the like; aryl or hetero-atom substituted aryl of from 5 to 20 carbon atoms, for example, phenyl and naphthyl, furyl, thienyl, pyridyl, quinolinyl and other heterocyclic systems; or halo such as chloro, fluoro; or atoms necessary to complete a fused aromatic ring.

Illustrative of the useful substituted oxadiazoles are the following:

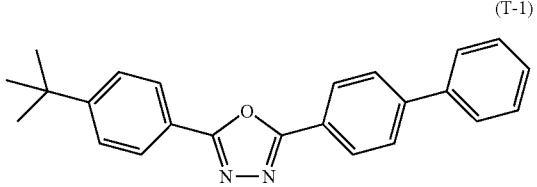

(T-1)

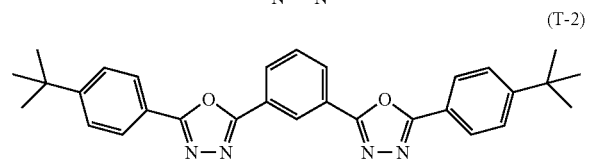

(T-2)

The electron-transporting material may also be selected from substituted 1,2,4-triazoles according to formula (U):

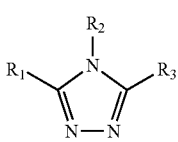

(U)

wherein:

$R_1$, $R_2$ and $R_3$ are independently hydrogen, alkyl group, aryl or substituted aryl group, and at least one of $R_1$-$R_3$ is aryl group or substituted aryl group. An example of a useful triazole is 3-phenyl-4-(1-naphtyl)-5-phenyl-1,2,4-triazole represented by formula (U-1):

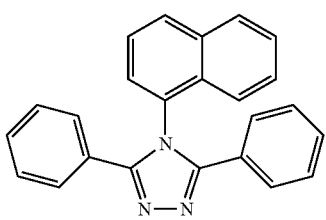

(U-1)

The electron-transporting material may also be selected from substituted 1,3,5-triazines. Examples of suitable materials are:

2,4,6-tris(diphenylamino)-1,3,5-triazine;
2,4,6-tricarbazolo-1,3,5-triazine;

2,4,6-tris(N-phenyl-2-naphthylamino)-1,3,5-triazine;
2,4,6-tris(N-phenyl-1-naphthylamino)-1,3,5-triazine;
4,4',6,6'-tetraphenyl-2,2'-bi-1,3,5-triazine;
2,4,6-tris([1,1':3',1"-terphenyl]-5'-yl)-1,3,5-triazine.

In addition, any of the metal chelated oxinoid compounds including chelates of oxine itself (also commonly referred to as 8-quinolinol or 8-hydroxyquinoline) of Formula (O) useful as host materials in a LEL are also suitable for use in the ETL.

Some metal chelated oxinoid compounds having high triplet energy can be particularly useful as an electron-transporting materials. Particularly useful aluminum or gallium complex host materials with high triplet energy levels are represented by Formula (V).

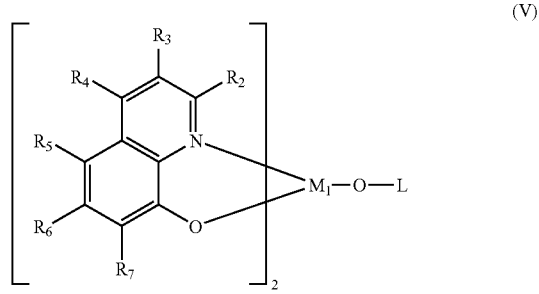

In Formula (V), $M_1$ represents Al or Ga. $R_2$-$R_7$ represent hydrogen or an independently selected substituent. Desirably, $R_2$ represents an electron-donating group. Suitably, $R_3$ and $R_4$ each independently represent hydrogen or an electron donating substituent. A preferred electron-donating group is alkyl such as methyl. Preferably, $R_5$, $R_6$, and $R_7$ each independently represent hydrogen or an electron-accepting group. Adjacent substituents, $R_2$-$R_7$, may combine to form a ring group. L is an aromatic moiety linked to the aluminum by oxygen, which may be substituted with substituent groups such that L has from 6 to 30 carbon atoms.

Illustrative of useful chelated oxinoid compounds for use in the ETL is Aluminum(III)bis(2-methyl-8-hydroxyquinoline)-4-phenylphenolate[alias, Balq].

The same anthracene derivatives according to formula (P) useful as host materials in the LEL can also be used in the ETL.

The thickness of the ETL is in the range of from 5 nm to 200 nm, preferably, in the range of from 10 nm to 150 nm.

Electron Injection Layer

The organic lithium compound of the invention is typically located in the EIL 138. The EIL may be composed only of the organic lithium compound, which is preferred, or there may be other materials present. For example, the EIL may be an n-type doped layer containing at least one electron-transporting material as a host and at least one n-type dopant. The dopant is capable of reducing the host by charge transfer. The term "n-type doped layer" means that this layer has semiconducting properties after doping, and the electrical current through this layer is substantially carried by the electrons.

The host in the EIL may be an electron-transporting material capable of supporting electron injection and electron transport. The electron-transporting material can be selected from the electron-transporting materials for use in the ETL region as defined above.

The n-type dopant in the n-type doped EIL may be is selected from alkali metals, alkali metal compounds, alkaline earth metals, or alkaline earth metal compounds, or combinations thereof. The term "metal compounds" includes organometallic complexes, metal-organic salts, and inorganic salts, oxides and halides. Among the class of metal-containing n-type dopants, Li, Na, K, Rb, Cs, Mg, Ca, Sr, Ba, La, Ce, Sm, Eu, Tb, Dy, or Yb, and their compounds, are particularly useful. The materials used as the n-type dopants in the n-type doped EIL also include organic reducing agents with strong electron-donating properties. By "strong electron-donating properties" it is meant that the organic dopant should be able to donate at least some electronic charge to the host to form a charge-transfer complex with the host. Nonlimiting examples of organic molecules include bis(ethylenedithio)-tetrathiafulvalene (BEDT-TTF), tetrathiafulvalene (TTF), and their derivatives. In the case of polymeric hosts, the dopant is any of the above or also a material molecularly dispersed or copolymerized with the host as a minor component. Preferably, the n-type dopant in the n-type doped EIL includes Li, Na, K, Rb, Cs, Mg, Ca, Sr, Ba, La, Ce, Nd, Sm, Eu, Tb, Dy, or Yb, or combinations thereof The n-type doped concentration is preferably in the range of 0.01-20% by volume of this layer.

When the EIL is composed only of the organic lithium compound of the invention, the thickness of the EIL is typically less than 20 nm, and preferably in the range of less than 5 nm. When an n-type doped EIL is employed, the thickness is typically less than 200 nm, and preferably in the range of less than 150 nm.

Cathode

When light emission is viewed solely through the anode, the cathode 140 includes nearly any conductive material. Desirable materials have effective film-forming properties to ensure effective contact with the underlying organic layer, promote electron injection at low voltage, and have effective stability. Useful cathode materials often contain a low work function metal (<4.0 eV) or metal alloy. One preferred cathode material includes a Mg:Ag alloy as described in U.S. Pat. No. 4,885,221. Another suitable class of cathode materials includes bilayers including a thin inorganic EIL in contact with an organic layer (e.g., organic EIL or ETL), which is capped with a thicker layer of a conductive metal. Here, the inorganic EIL preferably includes a low work function metal or metal salt and, if so, the thicker capping layer does not need to have a low work function. One such cathode includes a thin layer of LiF followed by a thicker layer of Al as described in U.S. Pat. No. 5,677,572. Other useful cathode material sets include, but are not limited to, those disclosed in U.S. Pat. Nos. 5,059,861, 5,059,862, and 6,140,763.

When light emission is viewed through the cathode, cathode 140 should be transparent or nearly transparent. For such applications, metals should be thin or one should use transparent conductive oxides, or include these materials. Optically transparent cathodes have been described in more detail in U.S. Pat. Nos. 4,885,211, 5,247,190, 5,703,436, 5,608,287, 5,837,391, 5,677,572, 5,776,622, 5,776,623, 5,714,838, 5,969,474, 5,739,545, 5,981,306, 6,137,223, 6,140,763, 6,172,459, 6,278,236, 6,284,393, and EP 1 076 368. Cathode materials are typically deposited by thermal evaporation, electron beam evaporation, ion sputtering, or chemical vapor deposition. When needed, patterning is achieved through many well known methods including, but not limited to, through-mask deposition, integral shadow masking, for example as described in U.S. Pat. No. 5,276,380 and EP 0 732 868, laser ablation, and selective chemical vapor deposition.

Substrate

OLED 100 is typically provided over a supporting substrate 110 where either the anode 120 or cathode 140 can be in contact with the substrate. The electrode in contact with the substrate is conveniently referred to as the bottom electrode. Conventionally, the bottom electrode is the anode 120, but this invention is not limited to that configuration. The substrate can either be light transmissive or opaque, depending on the intended direction of light emission. The light transmissive property is desirable for viewing the EL emission through the substrate. Transparent glass or plastic is commonly employed in such cases. The substrate can be a complex structure comprising multiple layers of materials. This is typically the case for active matrix substrates wherein TFTs are provided below the OLED layers. It is still necessary that the substrate, at least in the emissive pixelated areas, be comprised of largely transparent materials such as glass or polymers. For applications where the EL emission is viewed through the top electrode, the transmissive characteristic of the bottom support is immaterial, and therefore the substrate can be light transmissive, light absorbing or light reflective. Substrates for use in this case include, but are not limited to, glass, plastic, semiconductor materials such as silicon, ceramics, and circuit board materials. Again, the substrate can be a complex structure comprising multiple layers of materials such as found in active matrix TFT designs. It is necessary to provide in these device configurations a light-transparent top electrode.

Deposition of Organic Layers

The organic materials mentioned above are suitably deposited through sublimation, but can be deposited from a solvent with an optional binder to improve film formation. If the material is a polymer, solvent deposition is usually preferred. The material to be deposited by sublimation can be vaporized from a sublimator "boat" often comprised of a tantalum material, e.g., as described in U.S. Pat. No. 6,237,529, or can be first coated onto a donor sheet and then sublimed in closer proximity to the substrate. Layers with a mixture of materials can utilize separate sublimator boats or the materials can be premixed and coated from a single boat or donor sheet. Patterned deposition can be achieved using shadow masks, integral shadow masks (U.S. Pat. No. 5,294,870), spatially-defined thermal dye transfer from a donor sheet (U.S. Pat. No. 5,851,709 and U.S. Pat. No. 6,066,357) and inkjet method (U.S. Pat. No. 6,066,357).

Organic materials useful in making OLEDs, for example organic hole-transporting materials, organic light-emitting materials doped with an organic electroluminescent components have relatively complex molecular structures with relatively weak molecular bonding forces, so that care must be taken to avoid decomposition of the organic material(s) during physical vapor deposition. The aforementioned organic materials are synthesized to a relatively high degree of purity, and are provided in the form of powders, flakes, or granules. Such powders or flakes have been used heretofore for placement into a physical vapor deposition source wherein heat is applied for forming a vapor by sublimation or vaporization of the organic material, the vapor condensing on a substrate to provide an organic layer thereon.

Several problems have been observed in using organic powders, flakes, or granules in physical vapor deposition: These powders, flakes, or granules are difficult to handle. These organic materials generally have a relatively low physical density and undesirably low thermal conductivity, particularly when placed in a physical vapor deposition source which is disposed in a chamber evacuated to a reduced pressure as low as $10^{-6}$ Torr. Consequently, powder particles, flakes, or granules are heated only by radiative heating from a heated source, and by conductive heating of particles or flakes directly in contact with heated surfaces of the source. Powder particles, flakes, or granules which are not in contact with heated surfaces of the source are not effectively heated by conductive heating due to a relatively low particle-to-particle contact area; This can lead to nonuniform heating of such organic materials in physical vapor deposition sources. Therefore, result in potentially nonuniform vapor-deposited organic layers formed on a substrate.

These organic powders can be consolidated into a solid pellet. These solid pellets consolidating into a solid pellet from a mixture of a sublimable organic material powder are easier to handle. Consolidation of organic powder into a solid pellet can be accomplished with relatively simple tools. A solid pellet formed from mixture comprising one or more non-luminescent organic non-electroluminescent component materials or luminescent electroluminescent component materials or mixture of non-electroluminescent component and electroluminescent component materials can be placed into a physical vapor deposition source for making organic layer. Such consolidated pellets can be used in a physical vapor deposition apparatus.

In one aspect, the present invention provides a method of making an organic layer from compacted pellets of organic materials on a substrate, which will form part of an OLED.

One preferred method for depositing the materials of the present invention is described in U.S. Pat. No. 7,611,587 and U.S. Pat. No. 7,288,286 where different source evaporators are used to evaporate each of the materials of the present invention. A second preferred method involves the use of flash evaporation where materials are metered along a material feed path in which the material feed path is temperature controlled. Such a preferred method is described in the following co-assigned patent applications: U.S. Pat. Nos. 7,232,588; 7,238,389; 7,288,285; 7,288,286; 7,625,601; and 7,165,340. Using this second method, each material may be evaporated using different source evaporators or the solid materials may be mixed prior to evaporation using the same source evaporator.

Encapsulation

Most OLED devices are sensitive to moisture and/or oxygen so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890.

OLED Device Design Criteria

For full color display, the pixelation of LELs can be needed. This pixelated deposition of LELs is achieved using shadow masks, integral shadow masks, U.S. Pat. No. 5,294,870, spatially defined thermal dye transfer from a donor sheet, U.S. Pat. Nos. 5,688,551, 5,851,709, and 6,066,357, and inkjet method, U.S. Pat. No. 6,066,357.

OLED devices of this invention can employ various well-known optical effects in order to enhance its properties if desired. This includes optimizing layer thicknesses to yield maximum light transmission, providing dielectric mirror structures, providing reflective layers or microcavity structures, replacing reflective electrodes with light-absorbing electrodes, providing anti-glare or anti-reflection coatings over the display, providing a polarizing medium over the display, or providing colored, neutral density, or color-conversion filters over the display. Filters, polarizers, and anti-glare or anti-reflection coatings may be specifically provided over the cover or as part of the cover.

Embodiments of the invention may provide EL devices that have good luminance efficiency, good operational stability, and reduced drive voltages. Embodiments of the invention may also give reduced voltage rises over the lifetime of the devices and can be produced with high reproducibility and consistently to provide good light efficiency. They may have lower power consumption requirements and, when used with a battery, provide longer battery lifetimes.

EXPERIMENTAL EXAMPLES

It should be understood that in the synthesis of organic molecules, particular synthetic pathways can give rise to molecules, either exclusively or as mixtures of molecules, which have the same molecular formulae but differ only in having a particular substituent located at a different site somewhere in the molecule. In other words, the molecules or the molecules in the mixtures may differ from each other by the arrangement of their substituents or more generally, the arrangement of some of their atoms in space. When this occurs, the materials are referred to as isomers. A broader definition of an isomer can be found in *Grant and Hackh's Chemical Dictionary, Fifth Edition, McGraw-Hill Book Company, page* 313. The synthetic pathway outlined for Example 2 is an example of a pathway that can give rise to isomers by virtue of how the acetylene molecule reacts spatially with the unsymmetrical framework of the 8H-cyclopent[a]acenaphthylen-8-one entity of the second molecule. In this particular example, two isomers are possible, ETM2 and ETM7. It should be realized that the current invention includes not only examples of molecules represented by generic Formulae I, II and III and their specific molecular examples, but also includes all the isomers associated with these structures. In addition, examples of compounds of the invention and their isomers are not limited to those derived from a symmetrical or unsymmetrical 8H-cyclopent[a]acenaphthylen-8-one framework, but can also include other frameworks and methods of preparation that are useful in producing compounds of Formulae I, II and III.

Example 1

Inventive Compound, ETM1 was synthesized as outlined in the following scheme:

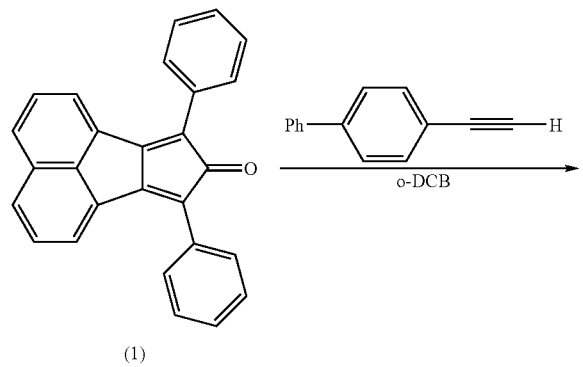

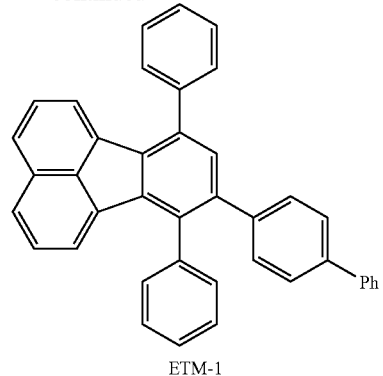

7,9-Diphenyl-8H-Cyclopent[a]acenaphthylen-8-one
(1)

7,9-Diphenyl-8H-Cyclopent[a]acenaphthylen-8-one, (aka Acecyclone), (1) was prepared according to the procedure of W. Dilthey, I ter Horst and W. Schommer; *Journal fuer Praktische Chemie* (*Leipzig*), 143, (1935), 189-210, in satisfactory yield.

8-[1,1'-Biphenyl]-4-yl-7,10-diphenylfluoranthene
(ETM1)

Acecyclone (12 g, 33.6 mMole) and 4-biphenylacetylene (9.0 g, 50.5 mMole) were heated to gentle reflux in ortho-dichlorobenzene (100 mL) for 2 hours. The reaction was then cooled, treated with methanol (20 mL) and stirred at room temperature for 1 hour. The resulting yellow solid was filtered of, washed well with methanol and dried. Yield of product ETM1, 17.4 g. Before use in device fabrication, ETM1 was sublimed at 220° C./10$^{-3}$ mm Hg.

Example 2

The inventive compound ETM2 was synthesized as outlined in the following scheme:

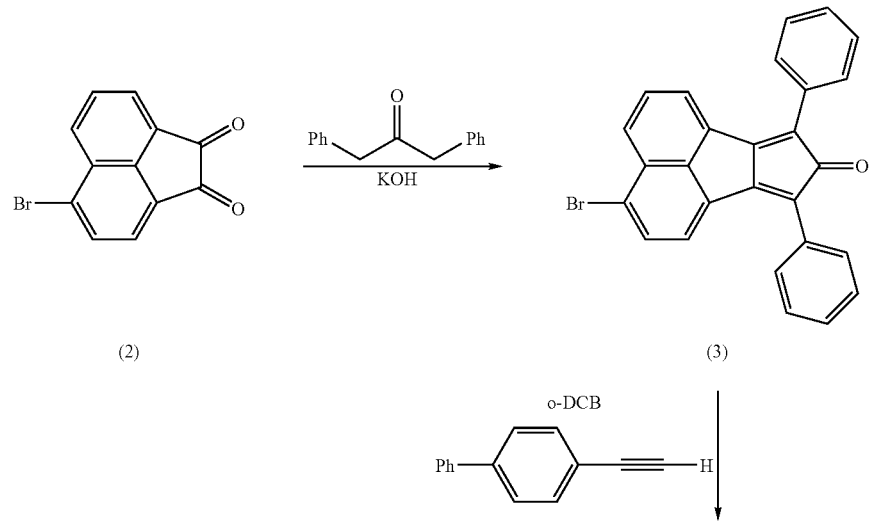

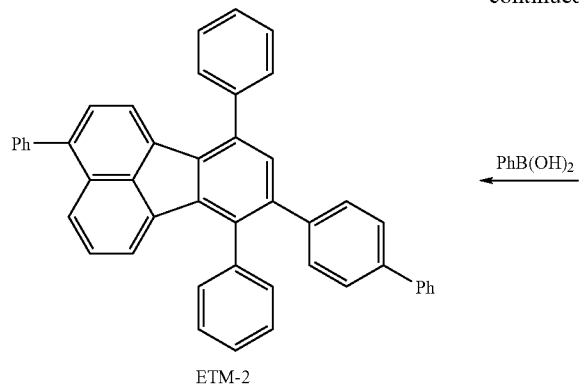

ETM-2

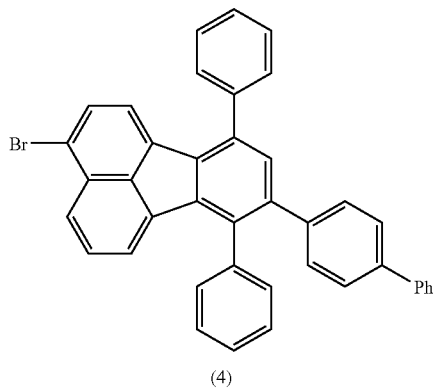

(4)

5-Bromoacenaphthenequinone (2)

5-Bromoacenaphthenequinone (2) was prepared according to the procedure of Gordon H. Rule and Samuel B. Thompson; *Journal of the Chemical Society*, (1937), 1761-1763, in satisfactory yield.

3-Bromo-7,9-diphenyl-8H-Cyclopent[a]acenaphthylen-8-one (3)

1,3-Diphenylacetone (17.5 g, 83 mMole) was dissolved in methanol (240 mL) and heated to 65° C. To the solution was added 5-bromoacenaphthenequinone (2), (20 g, 75 mMole). The resulting well-stirred suspension was then treated with 1M-methanolic KOH (100 ML, 100 mMole) at a fast drip rate, whereupon the dark colored product precipitated immediately. The mixture was then stirred at 65° C. for 1 hour, cooled and filtered. The black solid was washed well with methanol, ether and dried. Yield of product (3), (31 g).

3-Bromo-8-[1,1'-biphenyl]-4-yl-7,10-diphenylfluoranthene (4)

A mixture of 3-bromo-7,9-diphenyl-8H-Cyclopent[a] acenaphthylen-8-one, (20 g, 46 mMole) and 4-biphenylacetylene (12.3 g, 69 mMole) in ortho-dichlorobenzene (200 mL) were heated to gentle reflux for 2 hours. The resulting solution was cooled and treated with methanol (150 mL). During the course of 1 hour the product crystallized as a bright yellow solid. Yield of product (4), 22 g.

8-[1,1'-Biphenyl]-4-yl-3,7,10-triphenylfluoranthene (ETM2)

A mixture of 3-bromo-8-[1,1'-biphenyl]-4-yl-7,10-diphenylfluoranthene (7.2 g, 12 mMole), tetrakis(triphenylphosphine)palladium(0) (0.44 g, 3-mol-% based on the fluoranthene) and phenylboronic acid (1.8 g, 14 mMole), were suspended in toluene (100 mL) and stirred well with a mechanical stirrer. To this was then added 2M-Na$_2$CO$_3$ (14 mL) followed by ethanol (20 mL) and the mixture heated to gentle reflux for 1 hour. This mixture was then cooled to room temperature and treated with methanol (100 mL). The yellow solid was filtered off, washed well with water, methanol and ether, and then dried. Yield of product ETM2, 5.1 g. Before use in device fabrication, ETM2 was sublimed at 260° C/10$^{-3}$ mm Hg.

Example 3

Preparation of Devices 3.1 Through 3.8

A series of EL devices (3.1 through 3.8) were constructed in the following manner:

1. A glass substrate coated with an 85 nm layer of indium-tin oxide (ITO), as the anode, was sequentially ultrasonicated in a commercial detergent, rinsed in deionized water, and exposed to oxygen plasma for about 1 min.
2. Over the ITO was deposited a 1 nm fluorocarbon (CFx) hole-injecting layer (HIL) by plasma-assisted deposition of CHF$_3$ as described in U.S. Pat. No. 6,208,075.
3. Next a layer of hole-transporting material 4,4'-Bis[N-(1-naphthyl)-N-phenylamino]biphenyl (NPB) was deposited to a thickness of 95 nm.
4. A 20 nm light-emitting layer (LEL) composed of host material P-4, 1.5% of light emitting dopant FD-54, and the non-light emitting co-host ETM2, as recorded in Table 1, was then deposited.
5. A 35 nm electron-transporting layer (ETL) with ETM2, as shown in Table 1, was vacuum-deposited over the LEL.
6. An electron-injecting layer (EIL) as shown in Table 1, was vacuum deposited onto the ETL.
7. And finally, a 100 nm layer of aluminum was deposited onto the EIL, to form the cathode.

The above sequence completes the deposition of the EL devices. The devices were then hermetically packaged in a dry glove box for protection against ambient environment. The devices thus formed were tested for luminous efficiency at an operating current of 20 mA/cm$^2$ and the results are reported in Table 1.

TABLE 1

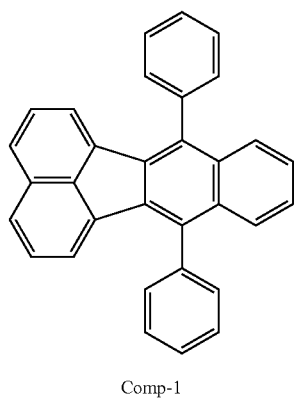 [SMILES: c1ccc(-c2c3c(c(-c4ccccc4)c4ccccc24)-c2cccc4cccc-3c24)cc1]

Comp-1

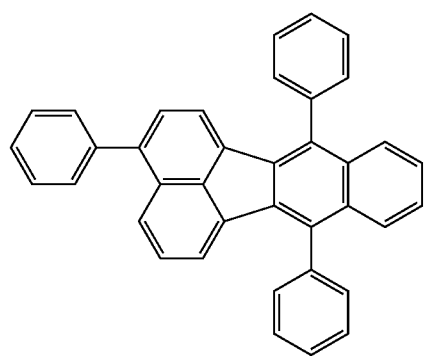

Comp-2

Experimental Results

| Example (Type) | LEL | ETL | EIL | Drive Volt. (Volts) | Efficiency (cd/A) |
|---|---|---|---|---|---|
| 3.1 (Comparative) | P-4 + 1.5% FD-54 | Comp-1 | EIM1 | 7.7 | 2.2 |
| 3.2 (Comparative) | P-4 + +2% Comp-1 + 1.5% FD-54 | Comp-1 | EIM1 | 7.7 | 2.5 |
| 3.3 (Comparative) | P-4 + +5% Comp-1 + 1.5% FD-54 | Comp-1 | EIM1 | 7.6 | 2.4 |
| 3.4 (Comparative) | P-4 + +10% Comp-1 + 1.5% FD-54 | Comp-1 | EIM1 | 7.6 | 2.1 |
| 3.5 (Comparative) | P-4 + +30% Comp-1 + 1.5% FD-54 | Comp-1 | EIM1 | 6.7 | 1.8 |
| 3.6 (Comparative | P-4 + 1.5% FD-54 | ETM2 | EIM1 | 5.1 | 5.6 |
| 3.7 (Inventive) | P-4 + 2% ETM2 + 1.5% FD-54 | ETM2 | EIM1 | 4.8 | 6.6 |
| 3.8 (Inventive) | P-4 + +5% ETM2 + 1.5% FD-54 | ETM2 | EIM1 | 5.3 | 7.5 |
| 3.9 (Inventive) | P-4 + +10% ETM2 + 1.5% FD-54 | ETM2 | EIM1 | 4.7 | 7.2 |
| 3.10 (Inventive) | P-4 + +30% ETM2 + 1.5% FD-54 | ETM2 | EIM1 | 4.3 | 7.4 |

Devices 3.1 to 3.5 of Table 1 are for comparative purposes and contain Comp-1 in the ETL. Device 3.1 contains no co-host in the LEL but P-4 as the only host. In devices 3.2 to 3.5 there are various volume % measures of the non-light emitting co-host Comp-1 in the LEL. Comp-1 is a material that falls outside the scope of the current invention. Device 3.6 is also a comparative device. It contains ETM2 in the ETL and P-4 as the only host in the LEL. Devices 3.7 to 3.10 are inventive and have ETM2 as a co-host in the LEL. The levels of ETM2 in the LEL are the same as the levels in the comparison devices 3.2 to 3.5. The organolithium complex as required by the invention, is present in both the comparative and inventive devices. From the table it can be seen that the performance of the inventive devices in terms of desirably higher luminance and lower drive voltage, is far superior to the comparison devices, at all levels of ETM2. In fact, when there is no co-host present in the LEL but P-4 alone, as shown in comparative device 3.6, inferior performance compared to those devices with the co-host is observed.

Example 4

Preparation of Devices 4.1 Through 4.4

A series of EL devices (4.1 through 4.4) were constructed in the following manner:

1. A glass substrate coated with an 85 nm layer of indium-tin oxide (ITO), as the anode, was sequentially ultrasonicated in a commercial detergent, rinsed in deionized water, and exposed to oxygen plasma for about 1 min.
2. Over the ITO was deposited a 1 nm fluorocarbon (CFx) hole-injecting layer (HIL) by plasma-assisted deposition of $CHF_3$ as described in U.S. Pat. No. 6,208,075.
3. Next a layer of hole-transporting material 4,4'-Bis[N-(1-naphthyl)-N-phenylamino]biphenyl (NPB) was deposited to a thickness of 144 nm.
4. A 40 nm light-emitting layer (LEL) composed of host material FD-5, 0.5% of light emitting dopant FD-46, and the non-light emitting co-host ETM2, as recorded in Table 2, was then deposited.
5. A 35 nm electron-transporting layer (ETL) of ETM2, was vacuum-deposited over the LEL.
6. A 35 nm electron-injecting layer (EIL) of EIM1, was vacuum deposited onto the ETL.
7. And finally, a 100 nm layer of aluminum was deposited onto the EIL, to form the cathode.

The above sequence completes the deposition of the EL devices. The devices were then hermetically packaged in a dry glove box for protection against ambient environment. The devices thus formed were tested for luminous efficiency at an operating current of 20 $mA/cm^2$ and the results are reported in Tables 2 and 3.

TABLE 2

Experimental Results

| Example (Type) | LEL | ETL | EIL | Drive Volt. (Volts) | Efficiency (cd/A) | $CIE_{x,y}$ |
|---|---|---|---|---|---|---|
| 4.1 (Comparative) | FD-5 + 0.5% FD-46 | ETM2 | EIM1 | 5.5 | 10.4 | 0.65, 0.34 |
| 4.2 (Inventive) | FD-5 + 10% ETM2 + 0.5% FD-46 | ETM2 | EIM1 | 4.8 | 12.2 | 0.66, 0.34 |
| 4.3 (Inventive) | FD-5 + 20% ETM2 + 0.5% FD-46 | ETM2 | EIM1 | 4.6 | 11.5 | 0.65, 0.35 |
| 4.4 (Inventive) | FD-5 + 50% ETM2 + 0.5% FD-46 | ETM2 | EIM1 | 4.9 | 11.8 | 0.66, 0.34 |

Figure 2:
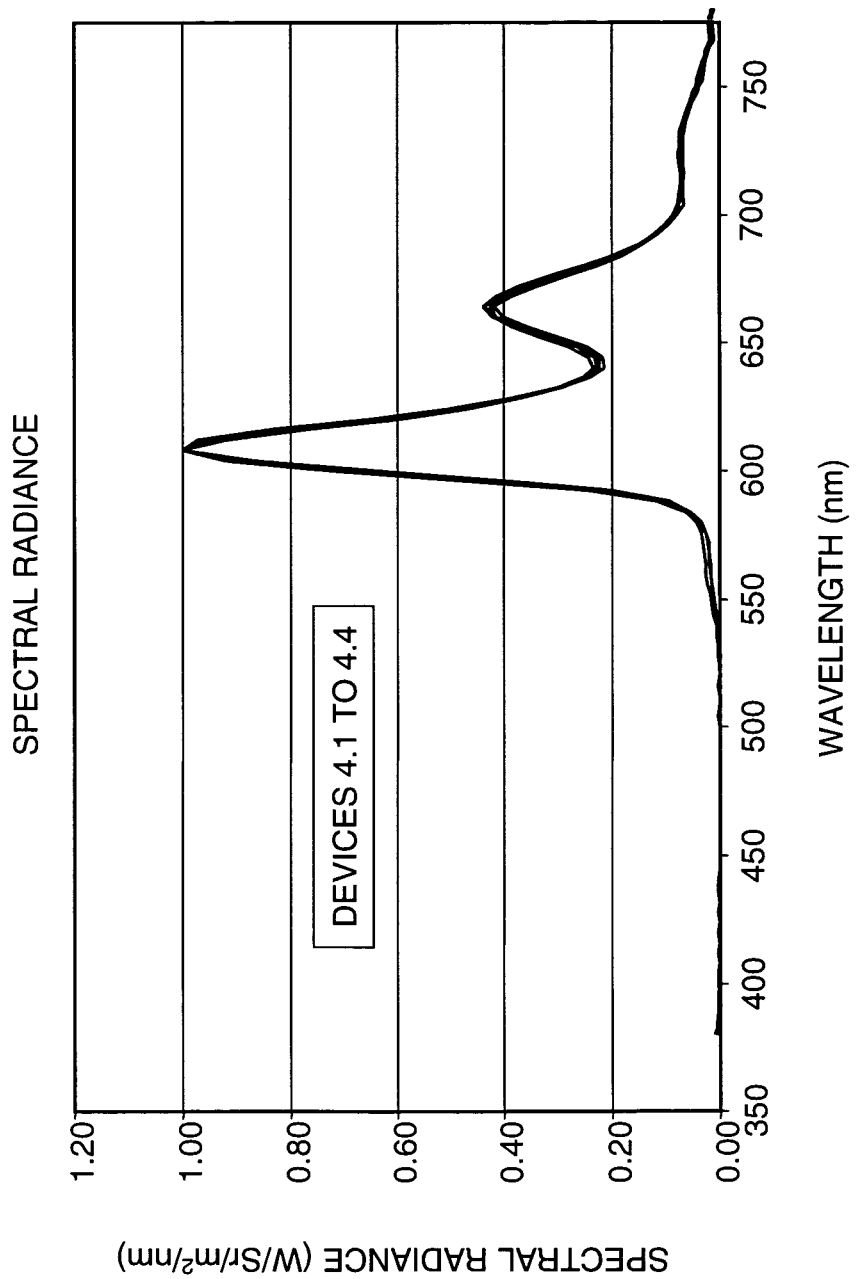
FIGS. 2-5 show the spectral response versus wavelength for comparative and inventive OLED devices with various host and dopant combinations.

Device 4.1 is a comparative device that is the same in all aspects to the inventive devices 4.2 to 4.4, except that device 4.1 has no ETM2 in the LEL and as such falls outside the scope of the current invention. It is clear from Table 2 that when ETM2 is in both the LEL and ETL with an organolithium complex as the EIM, the devices give better performance in terms of higher luminance efficiency and lower drive voltage. In addition to improvements in luminance and voltage performances, addition of co-host materials in the LEL also leads to improvements in fade stability. Table 3 shows the time in hours, it takes to reach a luminance efficiency of 50% of the original value when the devices are subjected to a current density of 80 mA/cm$^2$: the longer the device takes to reach the $T_{50}$ value, the more desirable it is. As can be seen from Table 3, the inventive devices 4.2 to 4.4 give greatly improved fade performance over the comparative device with no ETM2 in the LEL. As can be readily seen in FIG. 2 and the $CIE_{x,y}$ data, the addition of ETM2 causes no change in the emission spectra nor any emission in the blue region, thus indicating that ETM2 does not substantially emit light.

TABLE 3

Experimental Fade Results

| Example (Type) | $T_{50}$ @ 80 mA/cm$^2$ (hours) |
|---|---|
| 4.1 (Comparative) | 190 |
| 4.2 (Inventive) | 225 |
| 4.3 (Inventive) | 490 |
| 4.4 (Inventive) | 1506 |

Example 5

Preparation of Devices 5.1 through 5.5

A series of EL devices (5.1 through 5.5) was constructed in a similar manner to Example 4, except that EIM2 was used in place of EIM1 in the EIL layer of step 6. The results are reported in Table 4.

TABLE 4

Experimental Results

| Example (Type) | LEL | ETL | EIL | Drive Volt. (Volts) | Efficiency (cd/A) | $CIE_{x,y}$ |
|---|---|---|---|---|---|---|
| 5.1 (Comparative) | FD-5 + 0.5% FD-46 | ETM2 | EIM2 | 6.3 | 7.3 | 0.66, 0.34 |
| 5.2 (Inventive) | FD-5 + 10% ETM2 + 0.5% FD-46 | ETM2 | EIM2 | 6.6 | 9.2 | 0.66, 0.34 |
| 5.3 (Inventive) | FD-5 + 20% ETM2 + 0.5% FD-46 | ETM2 | EIM2 | 6.5 | 10.6 | 0.66, 0.34 |
| 5.4 (Inventive) | FD-5 + 50% ETM2 + 0.5% FD-46 | ETM2 | EIM2 | 6.4 | 11.6 | 0.66, 0.34 |
| 5.5 (Inventive) | FD-5 + 70% ETM2 + 0.5% FD-46 | ETM2 | EIM2 | 6.7 | 8.4 | 0.66, 0.34 |

Figure 3:
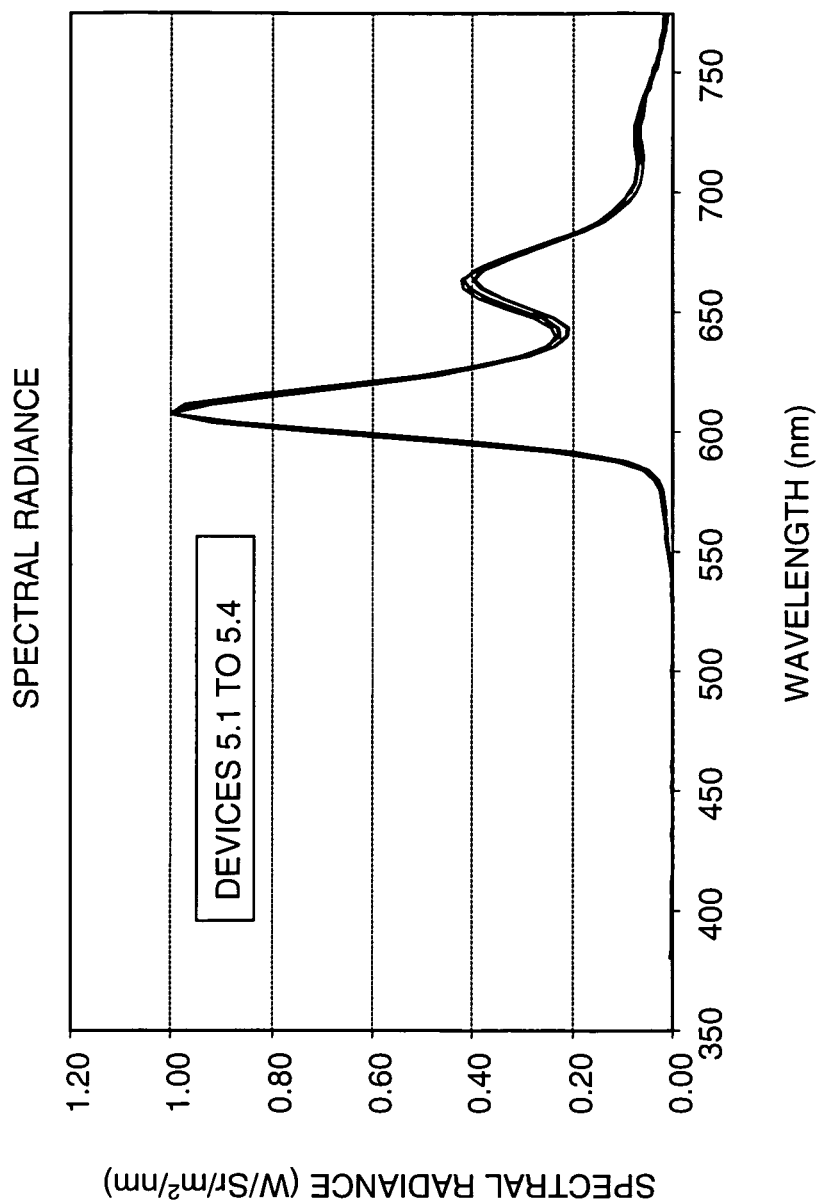

Device 5.1, which has no ETM2 in the LEL, is a comparative example. Devices 5.2 through 5.5 are inventive devices and are identical to 5.1 except that ETM2 is incorporated into the LEL of the inventive devices. From Table 4 it can be seen that the inventive devices give better luminance efficiency than the comparative device. As can be readily seen in FIG. 3 and the $CIE_{x,y}$ data, the addition of ETM2 causes no change in the emission spectra nor any emission in the blue region, thus indicating that ETM2 does not substantially emit light.

Example 6

Preparation of Devices 6.1 through 6.4

A series of EL devices (6.1 through 6.4) was constructed in a similar manner to Example 4, except that ETM1 was used in place of ETM2 in both the LEL and ETL of steps 4 and 5. The results are reported in Table 5.

TABLE 5

Experimental Results

| Example (Type) | LEL | ETL | EIL | Drive Volt. (Volts) | Efficiency (cd/A) | $CIE_{x,y}$ |
|---|---|---|---|---|---|---|
| 6.1 (Comparative) | FD-5 + 0.5% FD-46 | ETM21 | EIM1 | 5.6 | 9.1 | 0.66, 0.34 |
| 6.2 (Inventive) | FD-5 + 10% ETM21 + 0.5% FD-46 | ETM21 | EIM1 | 5.4 | 10.6 | 0.66, 0.34 |
| 6.3 (Inventive) | FD-5 + 20% ETM21 + 0.5% FD-46 | ETM21 | EIM1 | 5.4 | 11.4 | 0.66, 0.34 |
| 6.4 (Inventive) | FD-5 + 50% ETM21 + 0.5% FD-46 | ETM21 | EIM1 | 5.6 | 10.5 | 0.66, 0.34 |

Figure 4:
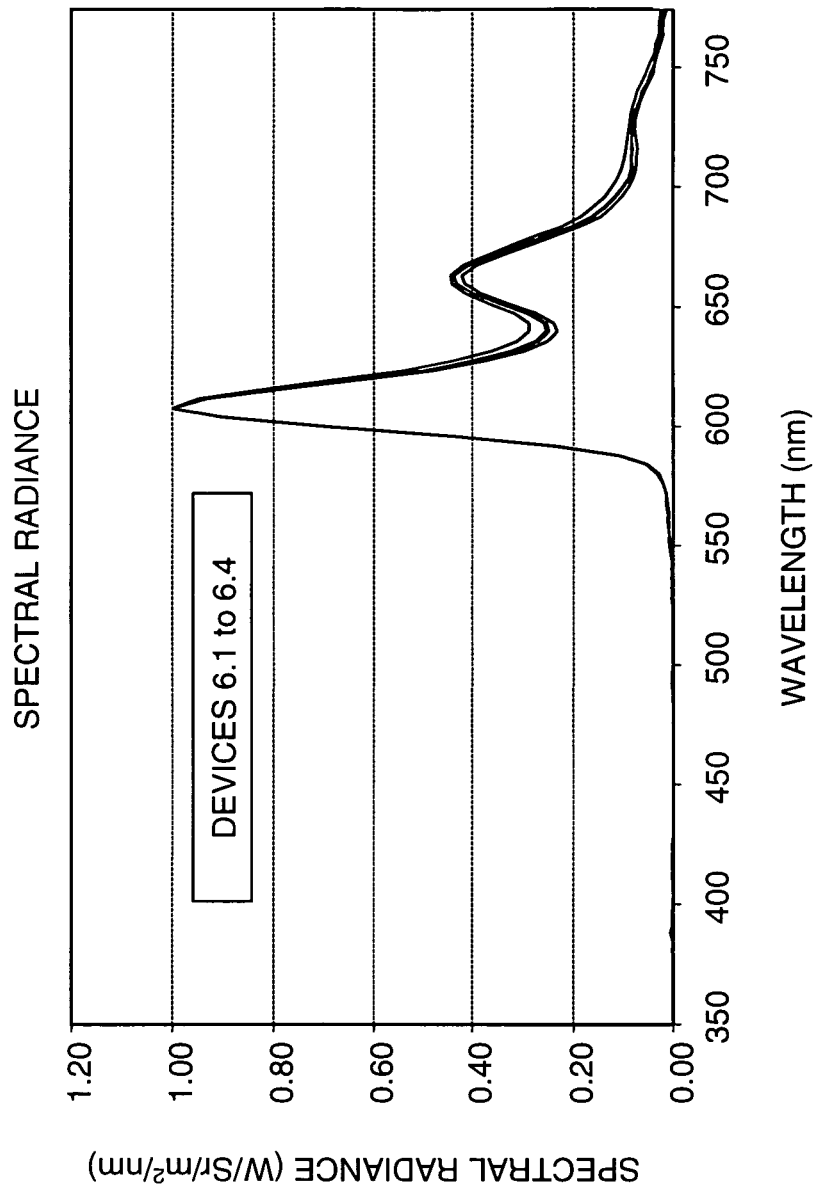

Device 6.1 has no ETM21 in the LEL and is a comparative example. Devices 6.2 through 6.4 are inventive devices and are identical to 6.1 except that co-host ETM21 is incorporated into the LEL of the inventive devices. From Table 5 it can be seen that the inventive devices give better luminance efficiency than the comparative device. As can be readily seen in FIG. 4 and the $CIE_{x,y}$ data, the addition of ETM2 causes no change in the emission spectra nor any emission in the blue region, thus indicating that ETM21 does not substantially emit light.

Example 7

Preparation of Devices 7.1 through 7.4

A series of EL devices (7.1 through 7.4) was constructed in a similar manner to Example 3, except that ETM21 was used in place of ETM2 in both the LEL and ETL of steps 4 and 5. The results are reported in Table 6.

TABLE 6

Experimental Results

| Example (Type) | LEL | ETL | EIL | Drive Volt. (Volts) | Efficiency (cd/A) | $CIE_{x,y}$ |
|---|---|---|---|---|---|---|
| 7.1 (Comparative) | P-4 + 1.5% FD-54 | ETM21 | EIM1 | 5.1 | 6.7 | 0.14, 0.15 |
| 7.2 (Inventive) | P-4 + 5% ETM21 + 1.5% FD-54 | ETM21 | EIM1 | 5.1 | 6.9 | 0.14, 0.14 |
| 7.3 (Inventive) | P-4 + 10% ETM21 + 1.5% FD-54 | ETM21 | EIM1 | 5.1 | 7.0 | 0.14, 0.14 |
| 7.4 (Inventive) | P-4 + 30% ETM21 + 1.5% FD-54 | ETM21 | EIM1 | 4.9 | 7.3 | 0.14, 0.15 |

Figure 5:
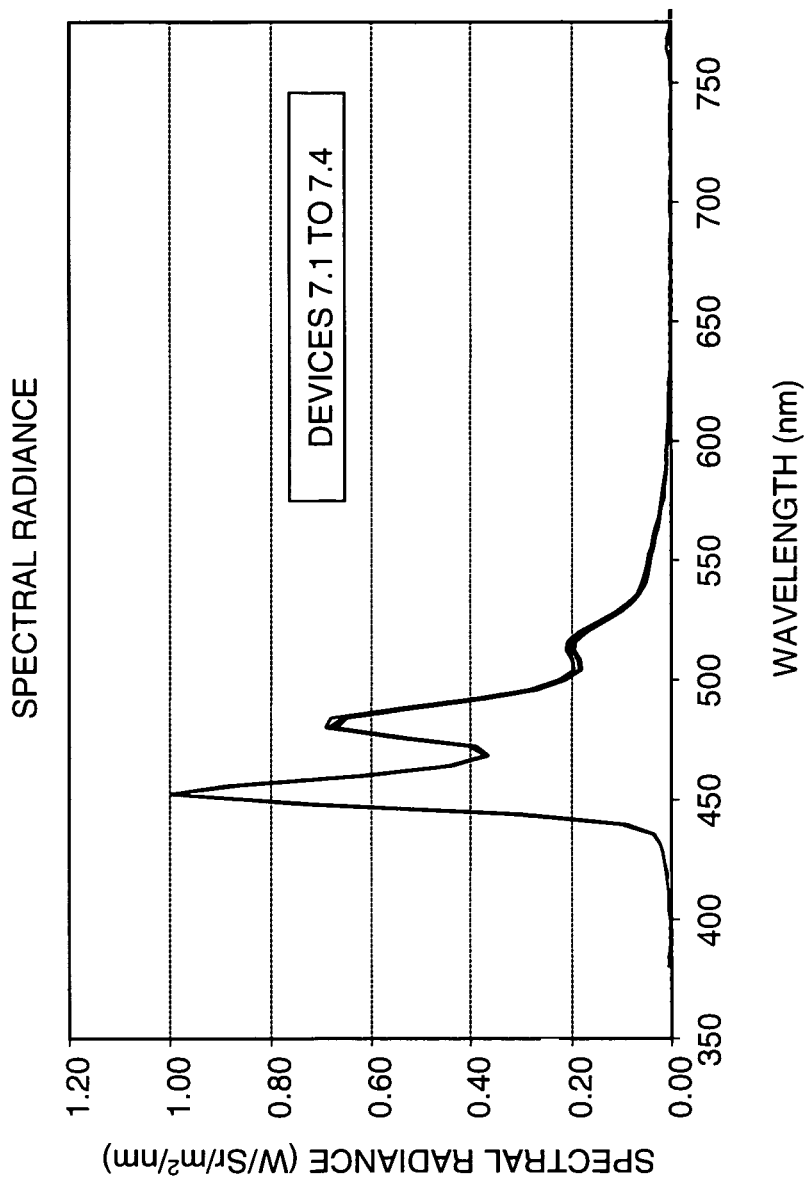

Device 7.1 has no ETM21 in the LEL and is a comparative example. Devices 7.2 through 7.4 are inventive devices and are identical to 7.1 except that ETM21 is incorporated into the LEL of the inventive devices. From Table 6 it can be seen that the inventive devices give better luminance efficiency than the comparative device. As can be readily seen in FIG. 5 and the $CIE_{x,y}$ data, the addition of ETM21 causes no change in the emission spectra, thus indicating that ETM2 does not substantially emit light.

Example 8

Preparation of Devices 8.1 through 8.4

A series of white EL devices (8.1 through 8.4) were constructed in the following manner:
1. A glass substrate coated with a 20 nm layer of indium-tin oxide (ITO), as the anode, was sequentially ultrasonicated in a commercial detergent, rinsed in deionized water and exposed to oxygen plasma for about 1 min.
2. Over the ITO was deposited a 10 nm hole-injecting layer (HIL) of dipyrazino[2,3-f:2',3'-h]quinoxalinehexacarbonitrile.
3. Next a layer of hole-transporting material 4,4'-Bis[N-(1-naphthyl)-N-phenylamino]biphenyl (NPB) was deposited to a thickness of 65 nm.
4. A 20 nm yellow light-emitting layer (LEL1) of 69% NPB host, 30% P-2 host and 1% dopant FD-57 was then deposited.
5. A 20 nm blue light-emitting layer (LEL2) of 98.5% P-2 host and 1.5% FD-54 dopant was then deposited.
6. A 31.5 nm electron-transporting layer (ETL) of 75% P-1 and 25% EIM2 was vacuum-deposited over the LEL.
7. A 3.5 nm electron-injecting layer (EIL) of EIM1 was then vacuum deposited onto the ETL.
8. And finally, a 100 nm layer of aluminum was deposited onto the EIL, to form the cathode.

The above sequence completes the deposition of the EL device 8.1. The device was then hermetically packaged in a dry glove box for protection against ambient environment.

Device 8.2 was prepared as device 8.1 except LEL2 of step 5 was composed of 98.5% ETN as the host and 1.5% FD-54 as the dopant. Device 8.3 was the same as device 8.1 except that the ETL of step 6 was replaced with 100% ETM2. Device 8.4 was the same as device 8.1 except that the ETL of step 6 was replaced with 100% ETM2.

The devices thus formed were tested for voltage and color at an operating current of 20 mA/cm$^2$ and the results are reported in Table 10.

TABLE 10

Device Results

| Example (Type) | LEL2 | ETL | EIL | Drive Volt. (Volts) | CIEx, y |
|---|---|---|---|---|---|
| 8.1 (Comparative) | P-2 + FD-54 | P-1 + EIM2 | EIM1 | 4.0 | 0.29, 0.28 |
| 8.2 (Inventive) | ETM2 + FD-54 | P-1 + EIM2 | EIM1 | 3.1 | 0.32, 0.35 |
| 8.3 (Comparative) | P-2 + FD-54 | ETM2 | EIM1 | 3.9 | 0.28, 0.27 |
| 8.4 (Inventive) | ETM2 + FD-54 | ETM2 | EIM1 | 3.3 | 0.34, 0.36 |

Figure 6:
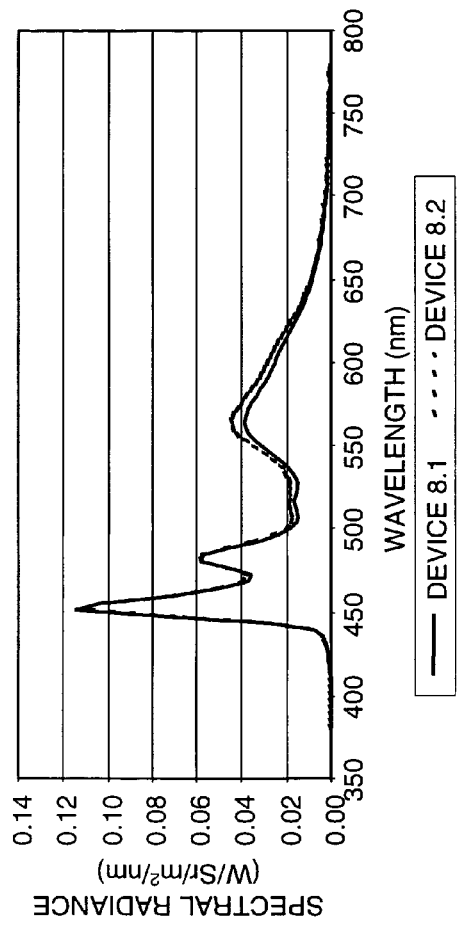
FIGS. 6-7 show the spectral response versus wavelength for experimental comparative and inventive white OLED devices.
Figure 7:
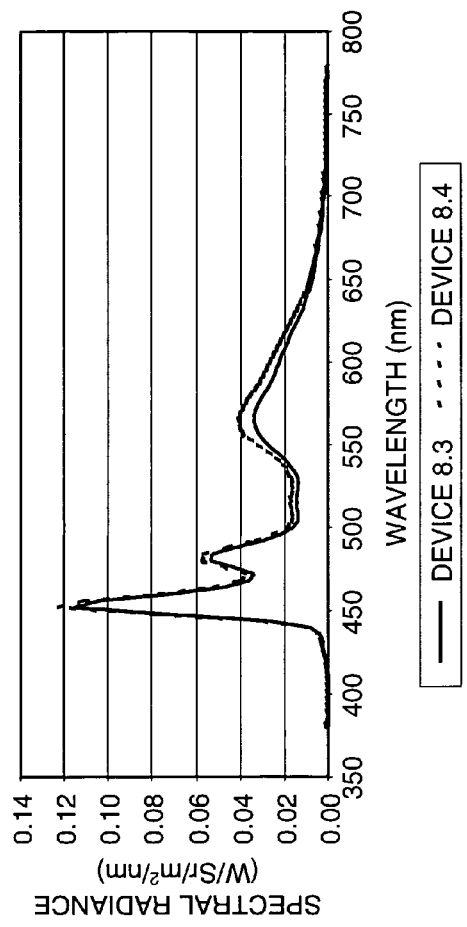

As seen in Table 10, the use of ETM-2 as a host in a blue light-emitting layer of a white OLED device lowers the voltage (device 8.2 versus 8.1). The additional use of ETM2 as the ETL layer (device 8.4 versus 8.3) further improves the voltage. The color emission of the devices with the inventive fluoranthenes are much closer to an ideal white (approximately 0.33, 0.33) than the check devices. FIGS. 6 and 7 show the spectral response versus wavelength for these devices demonstrating the excellent white color due to an improved height ratio between the blue, green and red peaks.

The invention has been described in detail with particular reference to certain preferred embodiments thereof, but it will be understood that variations and modifications can be effected within the spirit and scope of the invention. The patents and other publications referred to are incorporated herein in their entirety.

| PARTS LIST | |
|---|---|
| 100 | OLED |
| 110 | Substrate |
| 120 | Anode |
| 130 | Hole-Injecting layer (HIL) |
| 132 | Hole-Transporting layer (HTL) |
| 134 | Light-Emitting layer (LEL) |
| 135 | Hole-Blocking Layer (HBL) |
| 136 | Electron-Transporting layer (ETL) |
| 138 | Electron-Injecting layer (EIL) |
| 140 | Cathode |
| 150 | Voltage/Current Source |
| 160 | Electrical Connectors |

The invention claimed is:

1. An OLED device comprising a cathode, an anode, and therebetween:
   (a) a light emitting layer containing a non-light-emitting fluoranthene compound with a 7,10-diaryl substituted fluoranthene nucleus having no aromatic rings annulated to the fluoranthene nucleus;
   (b) an additional layer, containing an organic alkali metal compound; and
   (c) an electron-transporting layer including a polycyclic aromatic hydrocarbon,
   wherein the additional layer is located between the cathode and the electron transporting layer; and
   wherein the organic alkali metal compound is according to Formula (V):

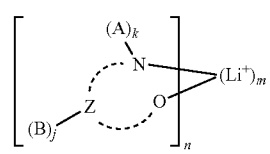

Formula (V)

wherein:
   Z and the dashed arc represent two to four atoms and the bonds necessary to complete a 5- to 7-membered ring with the lithium cation;
   each A represents hydrogen or a substituent and each B represents hydrogen or an independently selected substituent on the Z atoms, provided that two or more substituents may combine to form a fused ring or a fused ring system; and
   j is 0-3 and k is 1 or 2; and
   m and n are independently selected integers selected to provide a neutral charge on the complex, wherein the non-light-emitting fluoranthene compound and the polycyclic aromatic hydrocarbon are independently a fluoranthene compound of Formula (II):

Formula II

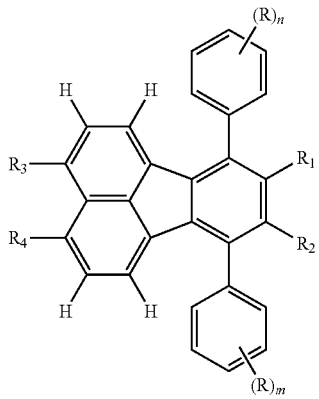

wherein:

$R_1$, $R_2$, $R_3$ and $R_4$ are independently hydrogen or an aromatic group containing 6 to 24 carbon atoms with the proviso that any adjacent $R_1$-$R_4$ is not part of an aromatic ring system annulated to the fluoranthene nucleus;

R is hydrogen or a substituent; and n and m are independently 1-5, and wherein the light emitting layer contains the fluoranthene host and a dopant chosen from anthracene, tetracene, xanthene, perylene, phenylene, dicyanomethylenepyran, thiopyran, polymethine compounds, pyrylium, thiapyrylium, arylpyrene, arylenevinylene, periflanthene, bis(azin$_x$l)methaneboron, distryeylbenzene, distyrylbiphenyl, distyrylamine and carbostyryl compounds.

2. The OLED device of claim 1, wherein the fluoranthene compound of formula (II) is according to Formula (IIIa) or (IIIb):

Formula (III-a)

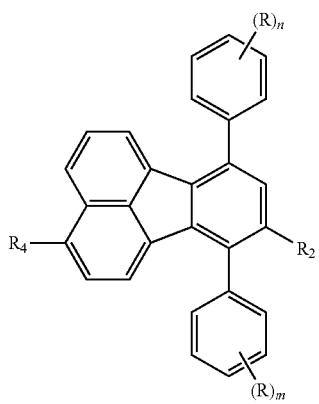

Formula (III-b)

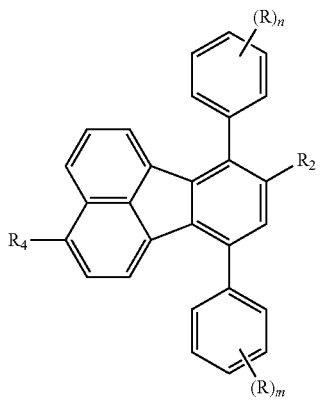

wherein:

$R_2$ and $R_4$ are independently hydrogen or an aromatic group containing 6 to 24 carbon atoms with the proviso that $R_2$ and $R_4$ cannot both be hydrogen nor can $R_2$ be joined with R to form an aromatic ring;

R is hydrogen or a substituent; and n and m are independently 1-5.

3. The OLED device of claim 1, wherein the A and B substituents of Formula (V) together form an additional ring system 4. The OLED device of claim 3 wherein the ring formed between the A and B substituents contains at least one heteroatom in addition to the nitrogen that is attached to A.

5. The OLED device of claim 1, where the organic alkali metal compound is chosen from:

EIM1

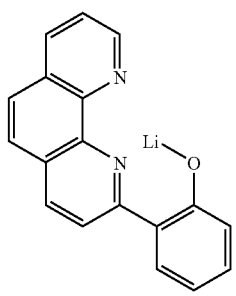

EIM2

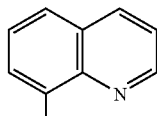

EIM3

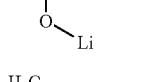

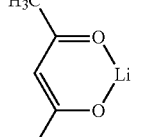

EIM4

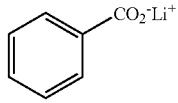

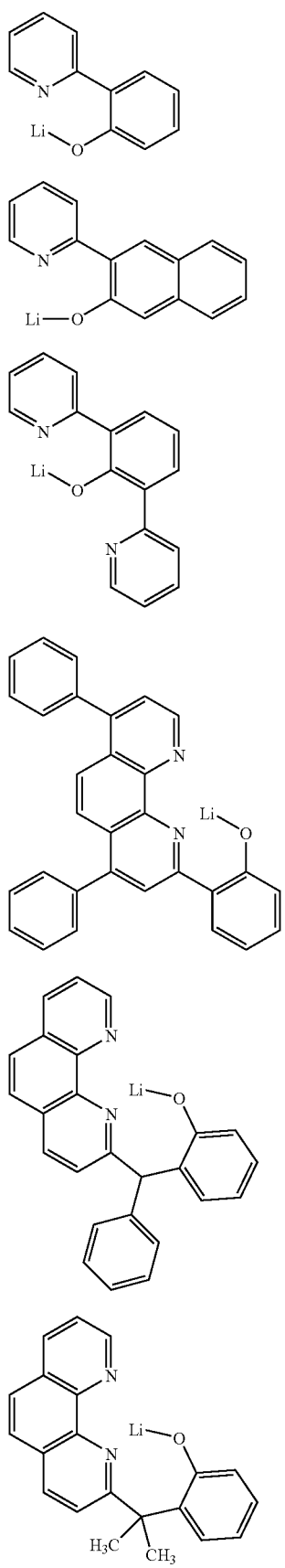
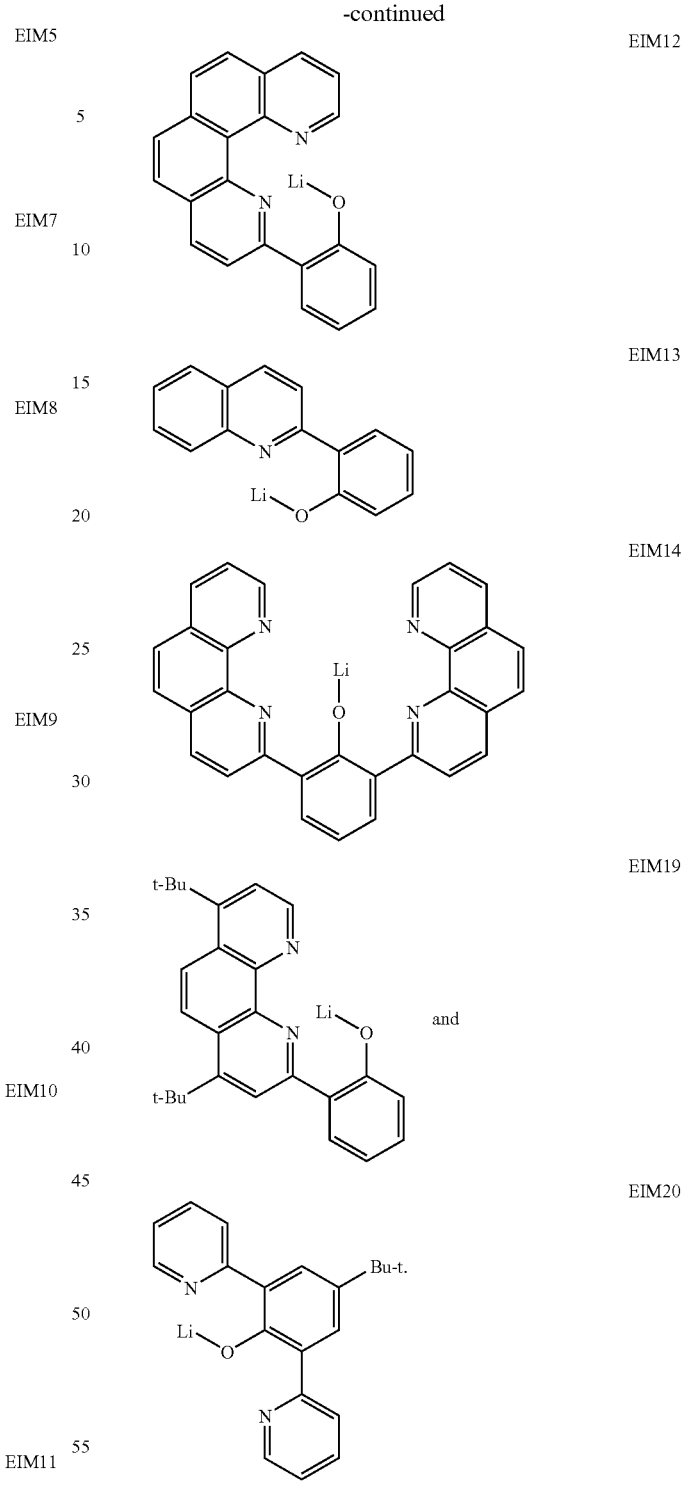
6. The OLED device of claim 1 wherein the electron-transporting layer additionally includes an alkali metal compound.
7. The OLED device of claim 6 wherein the alkali metal compound is an organic lithium compound according to Formula (V):

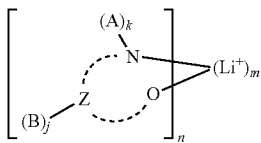

Formula (V)

wherein:

Z and the dashed arc represent two to four atoms and the bonds necessary to complete a 5- to 7-membered ring with the lithium cation;

each A represents hydrogen or a substituent and each B represents hydrogen or an independently selected substituent on the Z atoms, provided that two or more substituents may combine to form a fused ring or a fused ring system; and j is 0-3 and k is 1 or 2; and m and n are independently selected integers selected to provide a neutral charge on the complex.

8. The OLED device of claim 1 wherein the 7,10-diarylfluoranthene compound with no aromatic rings annulated to the nucleus in the light-emitting layer and the electron-transporting layer are the same.

9. The OLED device of claim 1 wherein the device emits white light.

10. The OLED device of claim 1, wherein the light-emitting layer containing the fluoranthene host emits blue light.

11. The OLED device of claim 1 wherein the light-emitting layer includes at least one additional non-light emitting host material and the total amount of all host materials present is at least 75% of volume of the layer.

12. The OLED device of claim 11 wherein the fluoranthene host comprises 50% or less of the total amount of all host materials present.

13. The OLED device of claim 12 where the additional host material is an anthracene compound.

14. A method of emitting light comprising applying an electric potential across the device of claim 1.

15. A display comprising the device of claim 1.

* * * * *